(12) United States Patent
Yaroslavsky et al.

(10) Patent No.: US 10,945,656 B2
(45) Date of Patent: Mar. 16, 2021

(54) DEVICE AND METHOD FOR IMAGING COLLAGEN STRUCTURE IN VIVO

(71) Applicant: The University of Massachusetts, Boston, MA (US)

(72) Inventors: Anna N. Yaroslavsky, North Andover, MA (US); Xin Feng, Lowell, MA (US)

(73) Assignee: THE UNIVERSITY OF MASSACHUSETTS, Boston, MA (US)

( * ) Notice: Subject to any disclaimer, the term of this patent is extended or adjusted under 35 U.S.C. 154(b) by 1025 days.

(21) Appl. No.: 14/780,907

(22) PCT Filed: Apr. 4, 2014

(86) PCT No.: PCT/US2014/033075
§ 371 (c)(1),
(2) Date: Sep. 28, 2015

(87) PCT Pub. No.: WO2014/165820
PCT Pub. Date: Oct. 9, 2014

(65) Prior Publication Data
US 2016/0066833 A1    Mar. 10, 2016

Related U.S. Application Data

(60) Provisional application No. 61/809,066, filed on Apr. 5, 2013.

(51) Int. Cl.
*A61B 5/00* (2006.01)
(52) U.S. Cl.
CPC ............ *A61B 5/443* (2013.01); *A61B 5/0071* (2013.01); *A61B 5/0077* (2013.01);
(Continued)

(58) Field of Classification Search
None
See application file for complete search history.

(56) References Cited

U.S. PATENT DOCUMENTS 6,587,711 B1    7/2003   Alfano et al.
6,694,176 B1 *  2/2004   Tsujita ................. A61B 5/0071
                                                          600/477
(Continued)

FOREIGN PATENT DOCUMENTS

WO    WO-9838907 A1    9/1998
WO    WO-2012/104784 A1    8/2012
WO    WO-2012/112911 A2    8/2012

OTHER PUBLICATIONS

International Search Report, International Application No. PCT/US2014/033075, International Filing Date Apr. 4, 2014, dated Sep. 12, 2014, 10 pages.

*Primary Examiner* — Bill Thomson
*Assistant Examiner* — Shahdeep Mohammed
(74) *Attorney, Agent, or Firm* — Brake Hughes Bellermann LLP

(57) ABSTRACT

The present invention relates to systems and methods or wide-field polarized imaging of the skin. Preferred embodiments of the invention provide quantitative characterization of collagen structures in the skin and can be used to monitor skin treatment. A preferred embodiment can comprise a handheld imaging device that generates polarized images at different depths beneath a dermal surface and a data processor to process image data.

28 Claims, 19 Drawing Sheets

(52) U.S. Cl.
CPC .......... *A61B 5/0082* (2013.01); *A61B 5/4848* (2013.01); *A61B 5/7271* (2013.01); *A61B 5/6835* (2013.01); *A61B 2560/0475* (2013.01)

(56) References Cited

U.S. PATENT DOCUMENTS

| | | | |
|---|---|---|---|
| 2004/0098070 A1* | 5/2004 | Mohr | A61B 18/20 607/89 |
| 2006/0184043 A1* | 8/2006 | Tromberg | A61B 5/0073 600/476 |
| 2006/0276713 A1* | 12/2006 | Maier | A61B 5/14532 600/473 |
| 2007/0024946 A1 | 2/2007 | Panasyuk et al. | |
| 2007/0173720 A1* | 7/2007 | Burdette | G01S 7/52071 600/438 |
| 2009/0080726 A1* | 3/2009 | Cotton | A61B 5/0059 382/128 |
| 2011/0144503 A1* | 6/2011 | Debreczeny | A61B 5/0059 600/476 |
| 2011/0301441 A1* | 12/2011 | Bandic | A61B 5/442 600/306 |
| 2012/0029348 A1* | 2/2012 | Yaroslavsky | G01N 21/6445 600/431 |
| 2015/0374309 A1* | 12/2015 | Farkas | G01N 21/21 600/473 |

* cited by examiner

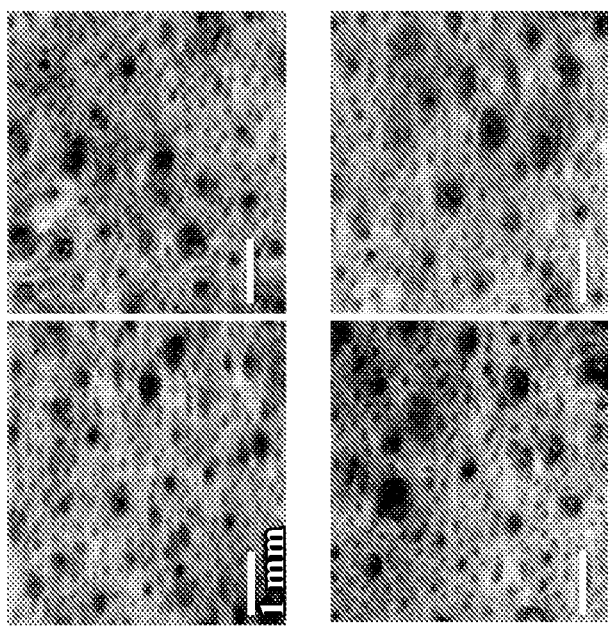
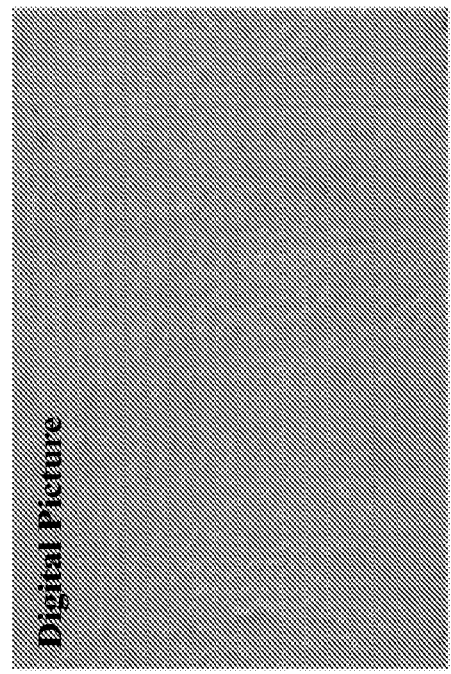
FIG. 6A
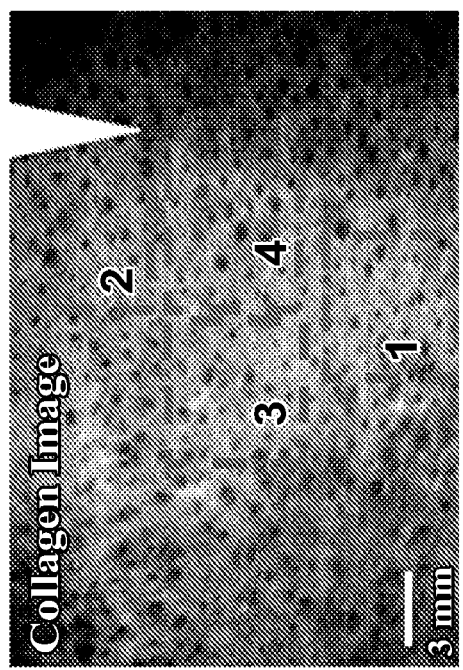
FIG. 6B
FIG. 6C

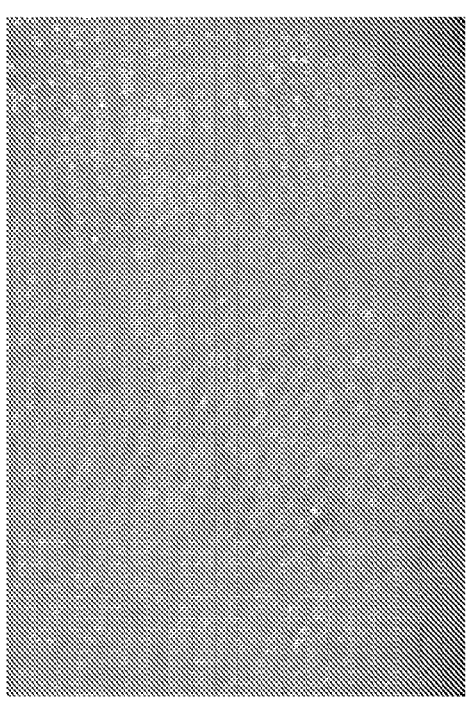
FIG. 7A
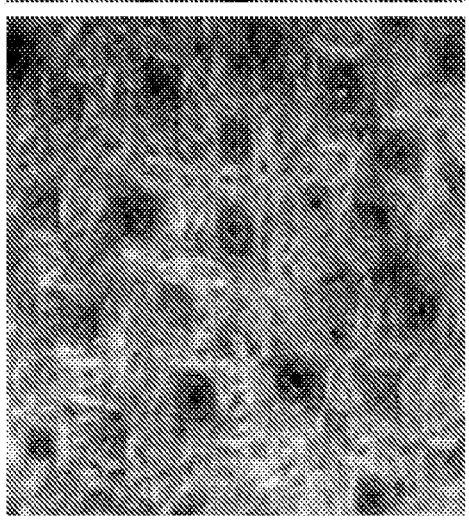
1
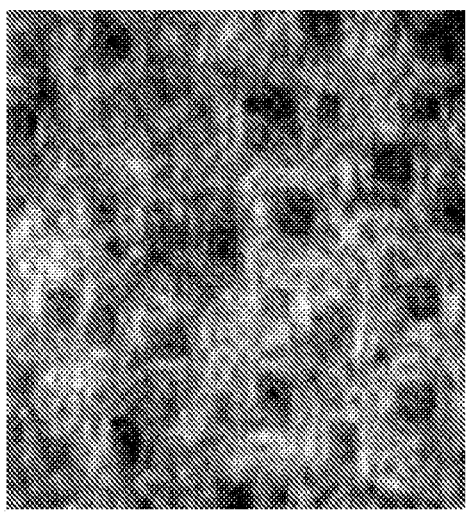
2
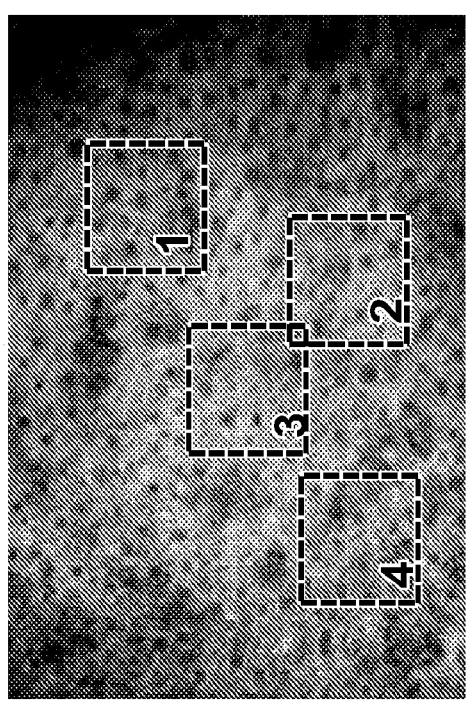
FIG. 7B
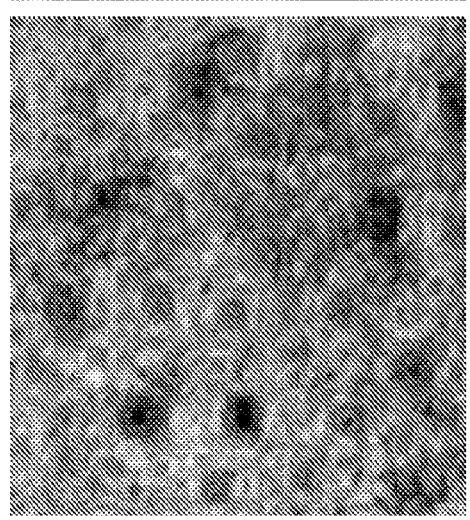
3
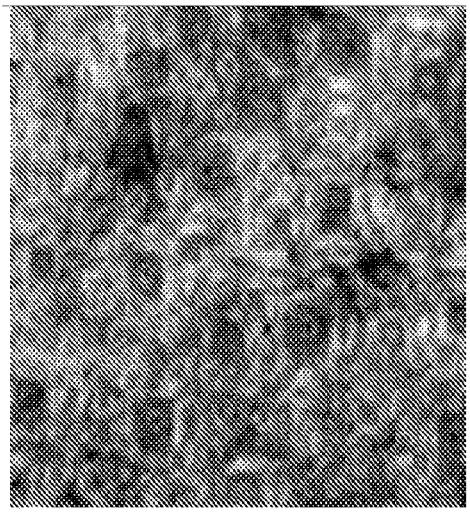
4
FIG. 7C

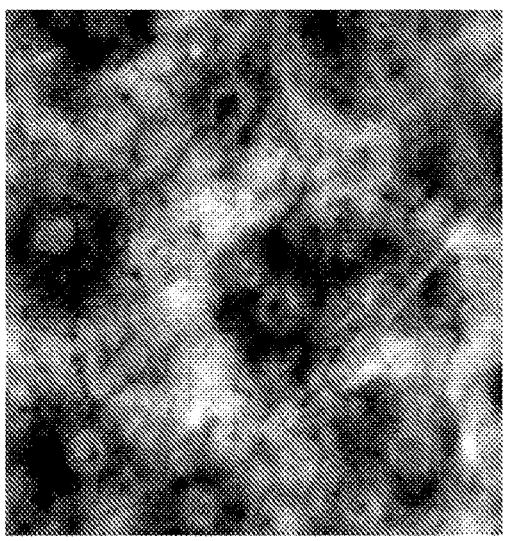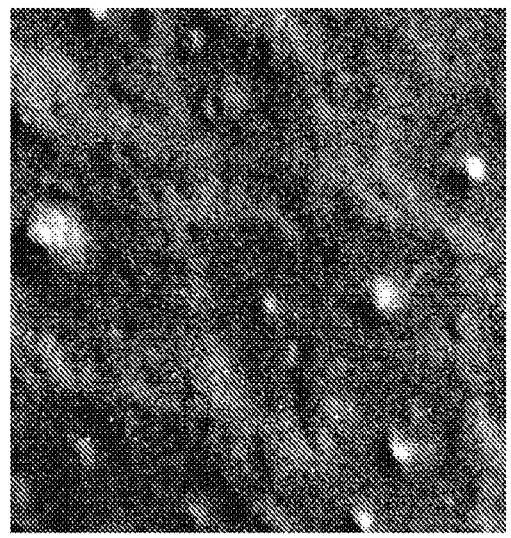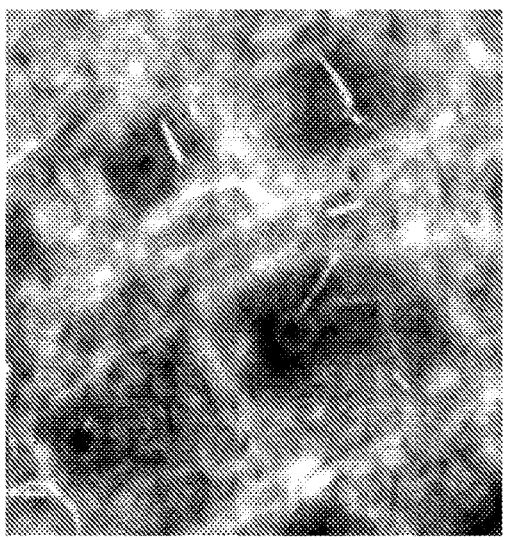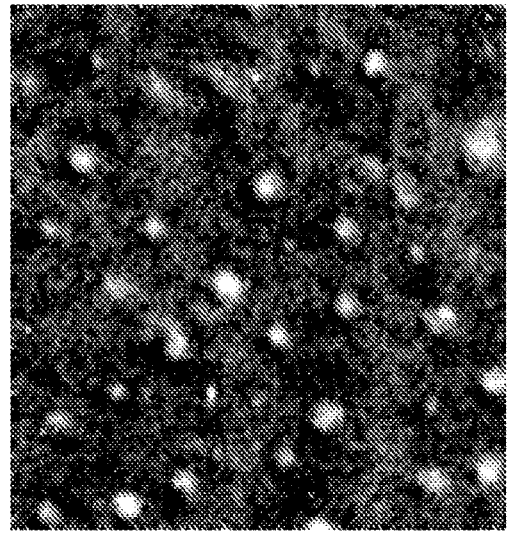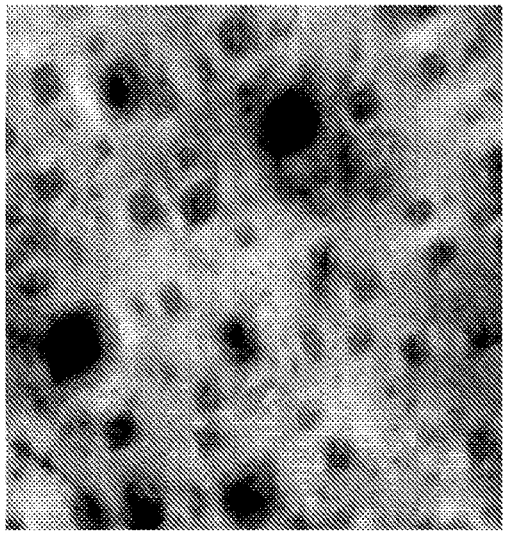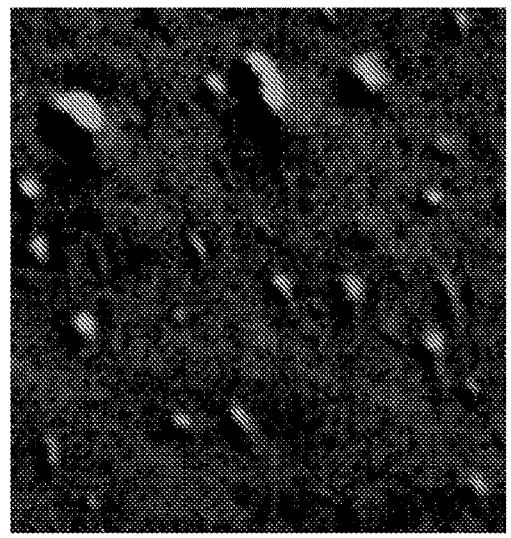

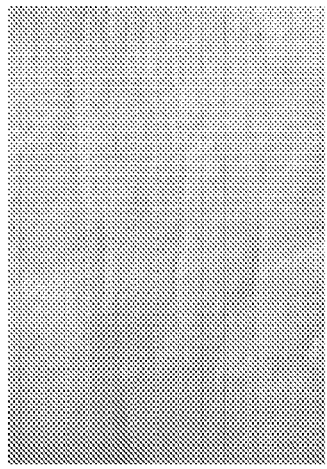
FIG. 12C
65 year old subject
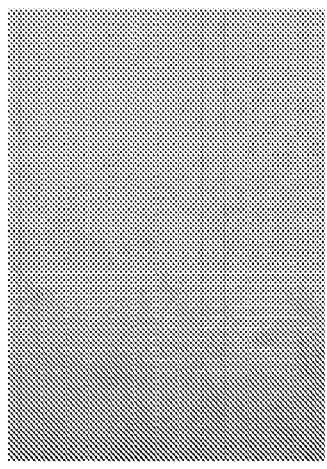
FIG. 12B
35 year old subject
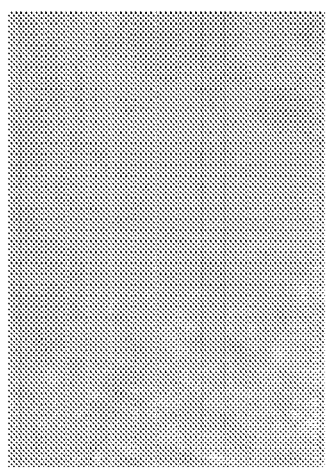
FIG. 12A
25 year old subject
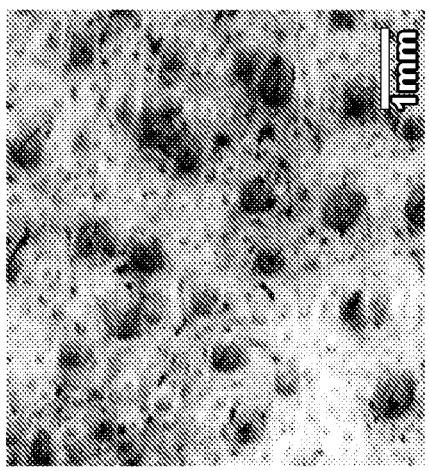
FIG. 12F
FIG. 12E
FIG. 12D

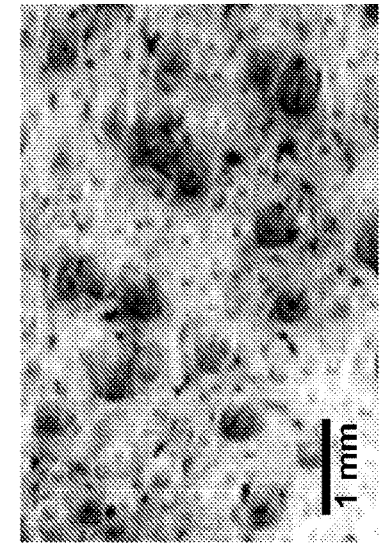
FIG. 16A Young
This Study
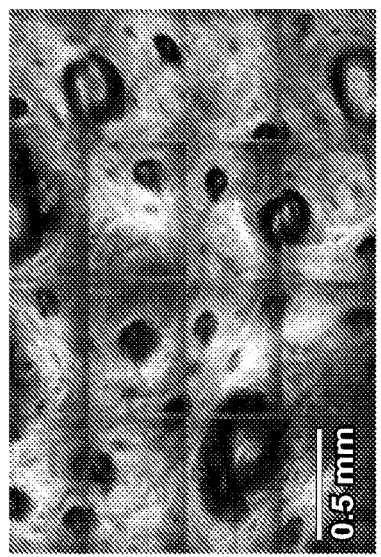
FIG. 16B Young
Second Harmonic Generation
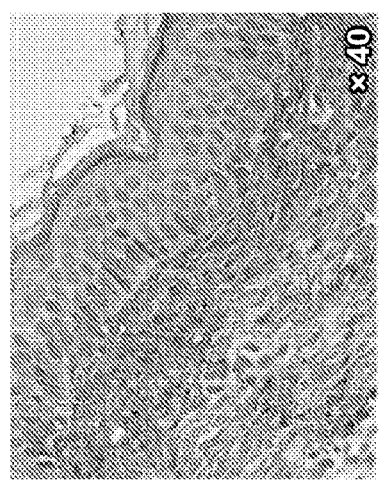
FIG. 16C Young
Immunohistochemical
Type III collagen
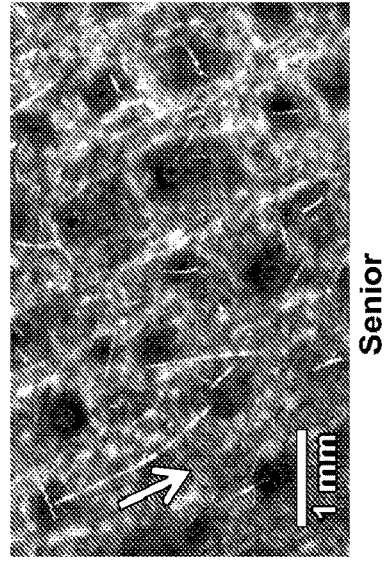
FIG. 16D Senior
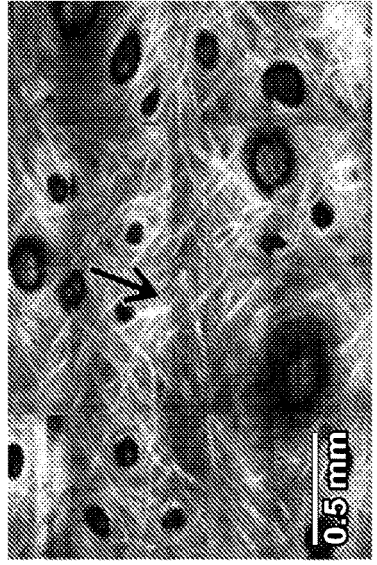
FIG. 16E Senior
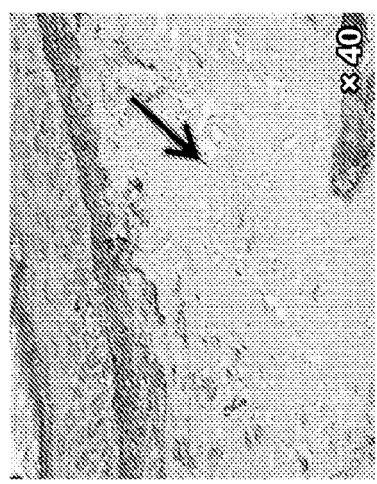
FIG. 16F Senior

DEVICE AND METHOD FOR IMAGING COLLAGEN STRUCTURE IN VIVO

CROSS REFERENCE TO RELATED APPLICATIONS

This application is a 35 U.S.C. § 371 national stage filing of International Application No. PCT/US2014/033075, filed on Apr. 4, 2014, which claims priority to U.S. Provisional Application No. 61/809,066, filed on Apr. 5, 2013, the entire contents of each of the applications being incorporated herein by reference.

BACKGROUND OF THE INVENTION

Skin is the first protection of human body against outside environment. Skin diseases and degeneration is related to sun exposure, working environment and personal habits, which can be observed in the change of internal structure of skin. Collagen, which is the major component of the dermal structure, is an important factor related to dermal changes. Thus it is critical to inspect collagen structure and quantitatively define status of skin. Histopathological and immunohistochemical studies are commonly used for diagnosing diseases and evaluating dermal changes. These techniques require biopsy, which may cause scarring and infection and cannot be performed either in vivo or in real time.

Several imaging techniques such as two photon microscopy, second harmonic generation and reflectance confocal microscopy are also used to interpret skin structure. Confocal microscopy is an imaging method with cellular resolution but due to the shallow imaging depths, this approach does not yield high contrast, high resolution images of collagen structure in vivo. Non-linear microscopy techniques such as two photon microscopy and second harmonic generation offer high-resolution morphological detail and deeper light penetration depth, but thus far it has not shown potential for in vivo visualization of dermal structure, due to high power densities required for imaging and the very small field of view. Thus, a continuing need exists for improvements for in vivo imaging of the skin.

SUMMARY OF THE INVENTION

The present invention relates to a polarization-sensitive, wide-field, reflectance imaging device and methods to image collagen structure and measure changes in dermal conditions. Preferred embodiments provide an in vivo rapid assessment of large skin areas with optical sectioning capability. An imaging detector and light source are positioned to illuminate the surface of a region of skin with one or more wavelengths of light. Polarized images are obtained at the tissue surface and at different selected depths beneath the dermal surface. In a preferred embodiment, the detector is spaced at a selected distance from an optical surface that can contact the surface of the skin to be imaged. A calibration reference can be used to enable quantification of characteristics of the tissue from the detected images.

A preferred embodiment can utilize a hand-carried device in which the imaging detector and light source can be housed to provide for portability and ease of use. An imaging aperture can be spaced at a fixed distance from a polarizing element to select a co-polarized or cross-polarized image and a lens that optically couples the image at the aperture onto the light receiving surface of the detector. The imaging aperture can be an optically transmissive element such as a glass window that can contact the skin. The entire aperture can be illuminated simultaneously to provide uniform illumination of the region of the skin being imaged in a single shot at each of a plurality of wavelengths.

BRIEF DESCRIPTION OF THE DRAWINGS

FIGS. 6A-6C show data and images for a subject including a digital picture of a subject; a 410 nm cross-polarization image; and four indicated regions of interests, respectively;

FIGS. 7A-7C show data and images for a subject including a digital picture of the skin, a 410 nm cross-polarization image; and four indicated regions of interests, respectively;

FIGS. 11A-11F show both reflectance and fluorescence images of various subjects;

FIGS. 12A-12F show image with the 1 mm bar indicating the size of the area imaged;

FIGS. 16A-16F show images of the collagen structure taken using various techniques;

DETAILED DESCRIPTION OF THE INVENTION

Figure 1A:
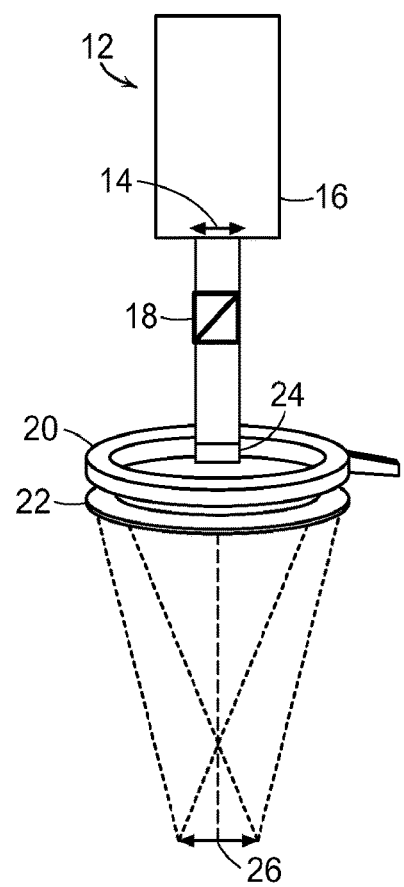
FIGS. 1A-1B show schematic illustrations of a wide-field imaging system in accordance with preferred embodiments of the invention.
Figure 1B:
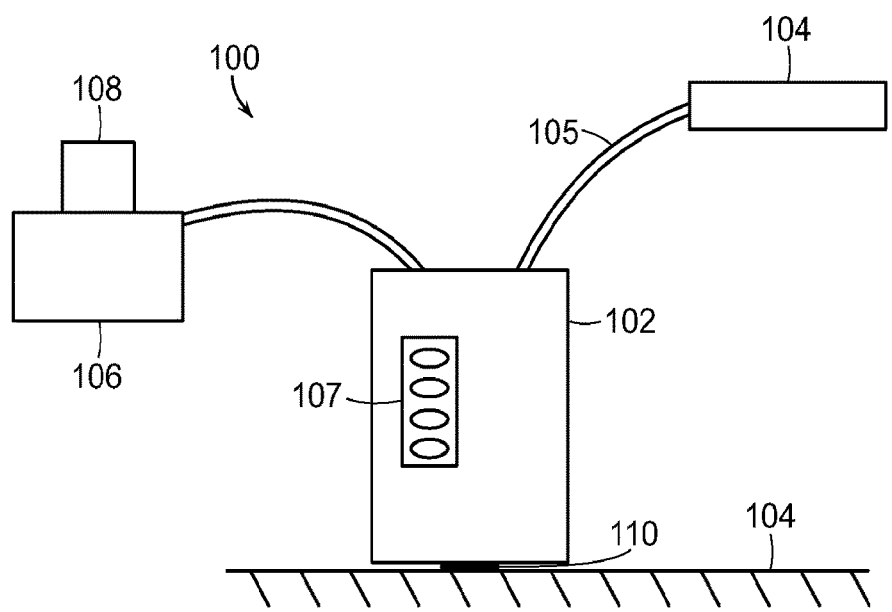

The images of collagen structures were acquired from the skin with intact epidermis and analyzed. Illustrated in FIG. 1A is a schematic view of the light delivery and detector elements and FIG. 1B shows a schematic view of the system including a handheld unit. As shown in FIG. 1A, the device 10 includes a camera housing 12 in which a detector 16 such as CCD or CMOS camera is positioned to receive a cross-polarized image 14 from polarizing beamsplitter 18 and a lens 24. Illumination can be provided by an LED ring 20, for example, that delivers polarized light using linear polarizer 22, onto a field of view 26 on a tissue surface. These elements can be integrated, as shown in FIG. 1B, into a handheld unit 102 of a portable diagnostic imaging system 100. Housing 102 can either include the light source such as the LED illumination of FIG. 1A, or can be connected to an external light source 104 with a fiber optic cable 105 as shown in FIG. 1B. The detector in housing 102 collects images from aperture 110 and sends image data over cable or wireless connection to a data processor such as computer 106 having a memory for storing images. Images and data can be displayed on electronic display 108 or sent via wireless or wired connection over a network such as the internet. Housing 102 can include the illuminator, lens, polarizers, window aperture 110, as described herein, and can be battery operated. An internal data processor and power regulator can also be included in housing 102 along with control panel 107 having buttons to control device operations.

In a preferred embodiment, a filtered lamp such as xenon or mercury arc lamp, or a halogen or metal halide light source can be combined with five narrow bandpass filters (full width at half maximum 10 nm, center wavelengths of 390 nm, 410 nm, 440 nm, 570 nm and 650 nm), for example. In another embodiment, the filtered lamp can be combined with four narrow bandpass filters (full width at half maximum of 10 nm, center wavelengths of 410 nm, 440 nm, 570 nm, and 650 nm). The filtered light is delivered with fiber optic cable configured into an annular array at a distal end to provide the illuminator. An array of lasers, such as laser diodes, can also be used. Light was delivered to the skin via a fiber-optic linearly polarizing ring-light illuminator with power density of 0.6 mW/cm$^2$ or less. Cross-polarized images were acquired using a CCD camera coupled with an objective lens (0.5× lens) and linearly polarizing filter. The linearly polarizing filter was introduced into the pathway of incident light and a polarizing beam splitter was introduced into the pathway of light collected by the camera.

Figure 2A:
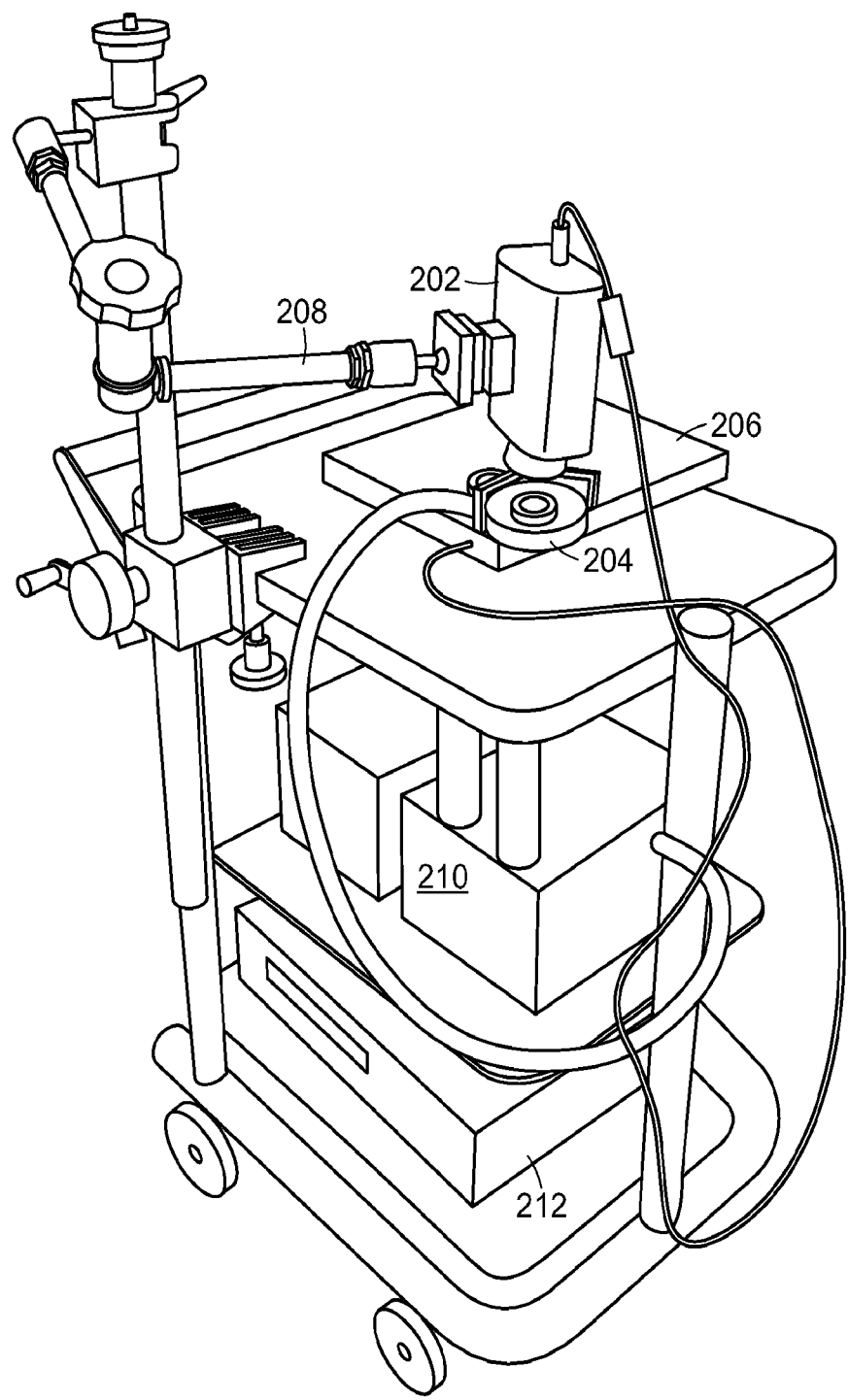
FIG. 2A illustrates a polarization enhanced reflectance imaging system in accordance with a preferred embodiment of the invention.
Figure 2B:
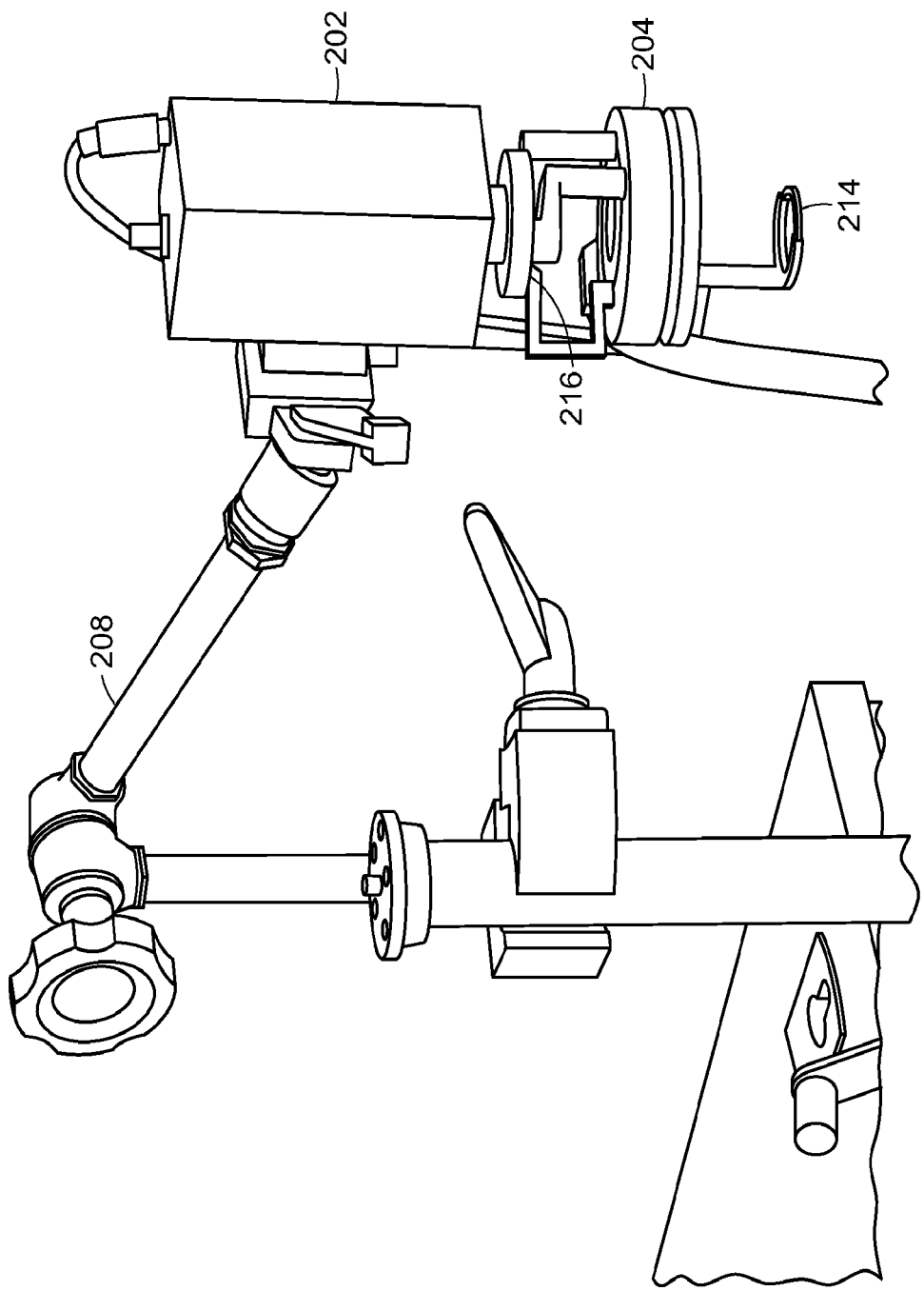
FIG. 2B is a view of the system including a spacer, an illuminator, an optical lens, a CCD camera, and an articulating arm.

The schematic of this system is illustrated in FIGS. 2A and 2B. System 200 of FIG. 2A includes an imaging system comprising a CCD camera 202 and an illuminator 204. The imaging system is operatively coupled to or is in communication with computer 206. The imaging system is coupled to an articulating arm 208. System 200 also includes a lamp 210 and controller 212 operatively coupled to the imaging system and computer 206. FIG. 2B illustrates a close-view of the system illustrated in FIG. 2A. The system of FIG. 2B includes CCD camera 202, illuminator 204, articulating arm 208, spacer 214 and optical lens 216. This system (illustrated in FIGS. 2A and 2B) allows acquisition of cross-polarized light images at selected wavelengths, including 410 nm, 440 nm, 570 nm, and 650 nm in the visible spectral range. This system also provides field of view of up to 50 mm×50 mm and lateral resolution down to the pixel size of the camera, in this embodiment, to 12 μm with the 0.5× objective lens. The imager (CCD camera and illuminator) was installed on an articulated arm to enable flexibility and comfort to the subjects. A spacer with the length equal to the focal length of the objective lens, with a sterile glass plate at the bottom of the spacer was employed to ensure proper focusing distance, flatten the skin surface and to minimize motion artifacts during imaging that can arise from patient movement, such as breathing. A calibrated reflectance reference was attached to the glass plate to enable quantitative assessment of the images. Refractive index matching gel was applied to skin surface to reduce refractive index mismatch between skin and glass plate and improve light coupling into the skin and back onto the detector.

Figure 3:
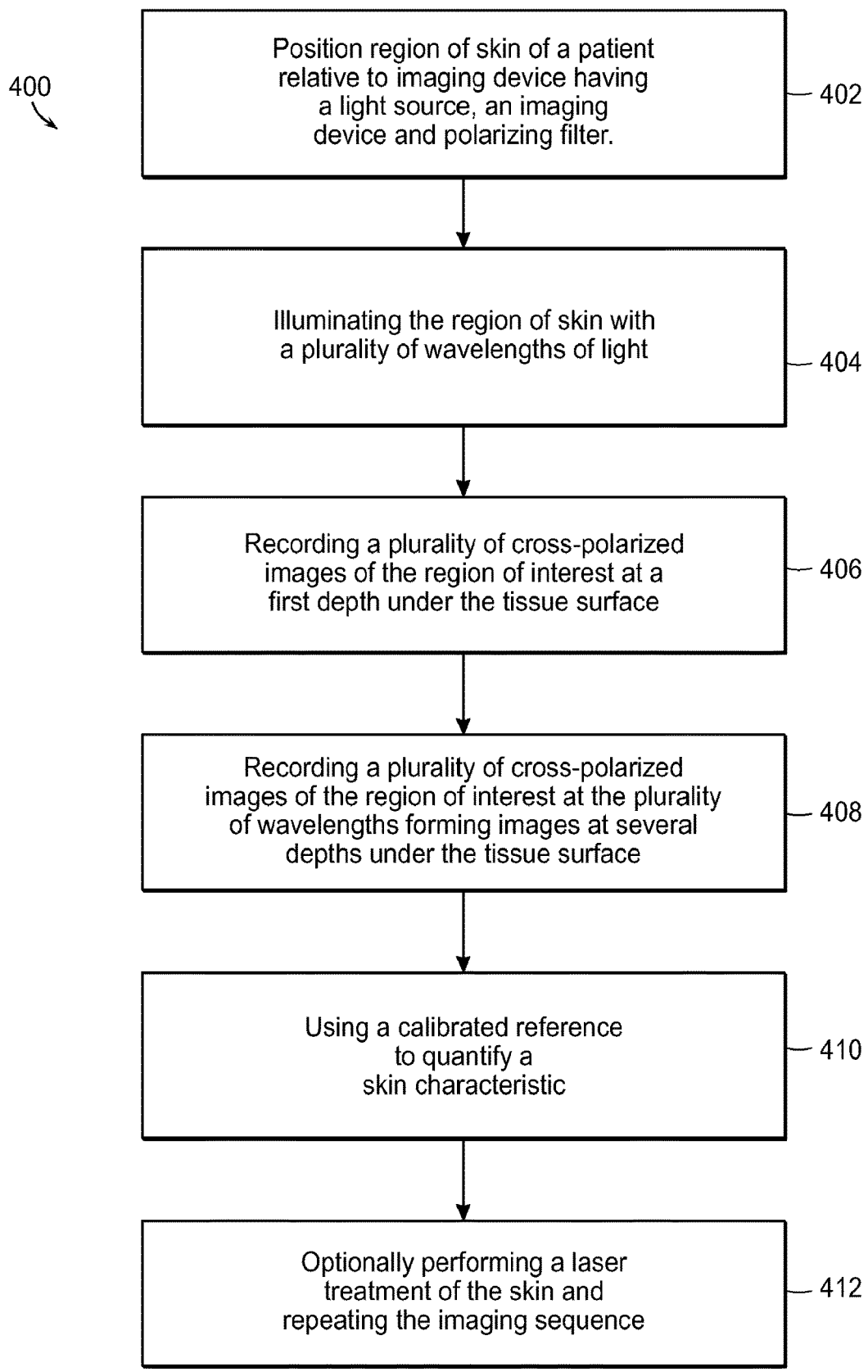
FIG. 3 is a process sequence for performing diagnostic imaging methods in accordance with preferred embodiments of the invention.
Figure 4:
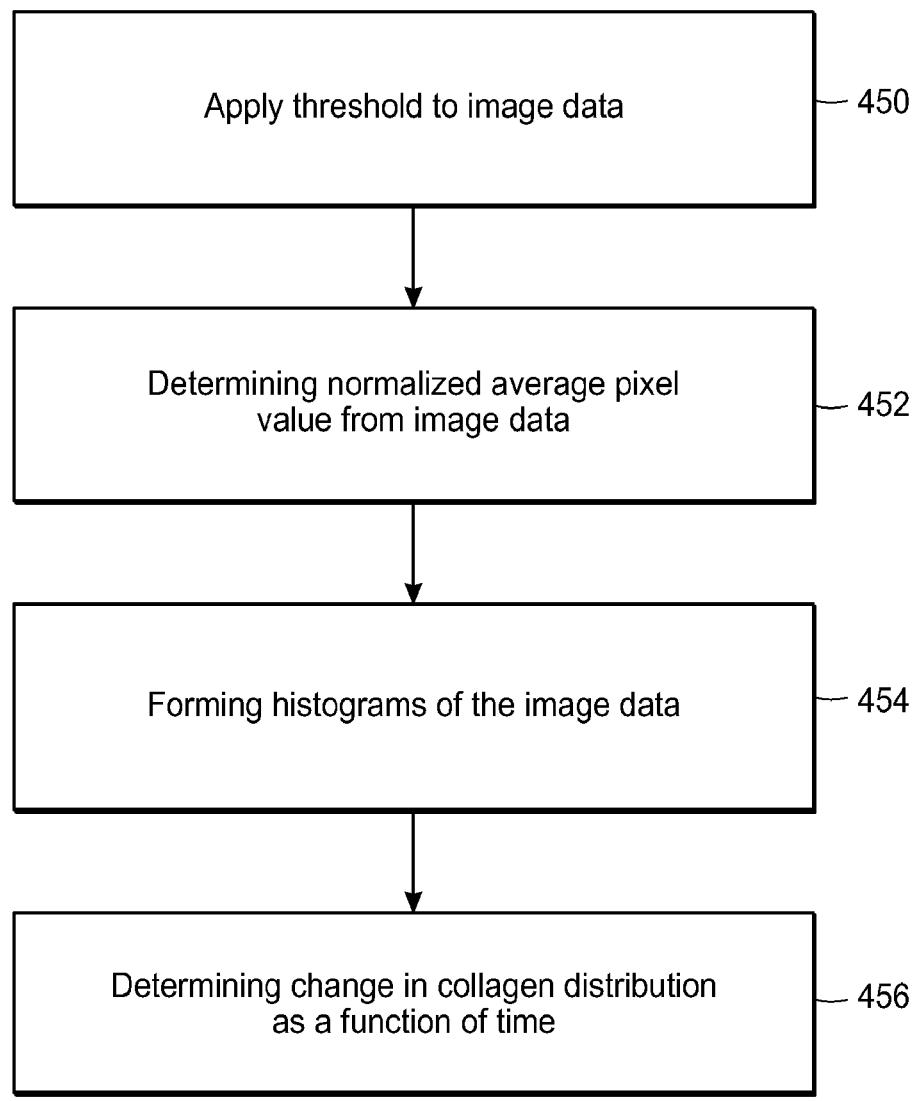
FIG. 4 is a process sequence illustrating an image processing method in accordance with the invention.

A method for imaging 400 a region of interest on the skin of a patient is shown in FIG. 3. The user first positions 402 the region of skin relative to the imaging device and light source to enable the acquisition of polarized images. A holder can be used to stabilize the region of skin and an articulating arm can be used to hold the imaging device housing. The region of skin is uniformly illuminated 404 to capture an image of the entire field of view in a single shot. A plurality of images can be recorded 406 at the tissue surface and at a first depth. Images can be recorded 408 at a deeper, or second depth by altering the illumination wavelength. A data processor can be used to process the image data using a calibrated reference and thereby generate quantitative data for a skin characteristic 410. Data such as the content and density of collagen, the size of individual collagen bundles and blood vessels can be measured. The images can have a field of view that ranges from 3 cm$^2$ to 20 cm$^2$, for example. The system can include an adjustable lens assembly to enable changing the area of the field of view. This process can be used with treatment methods to monitor 412 changes in the skin. After acquisition, the images were filtered using low pass and sharpen filters to reduce the noise and impact of scattering from the lower skin layers (such as lower blood plexus and subcutaneous fat) on the quality of collagen images. Further details regarding systems and methods of polarized imaging of tissue are described in International Application No. PCT/US2012/025678, filed Feb. 17, 2012, the entire contents of this application being incorporated herein by reference.

Figure 5A:
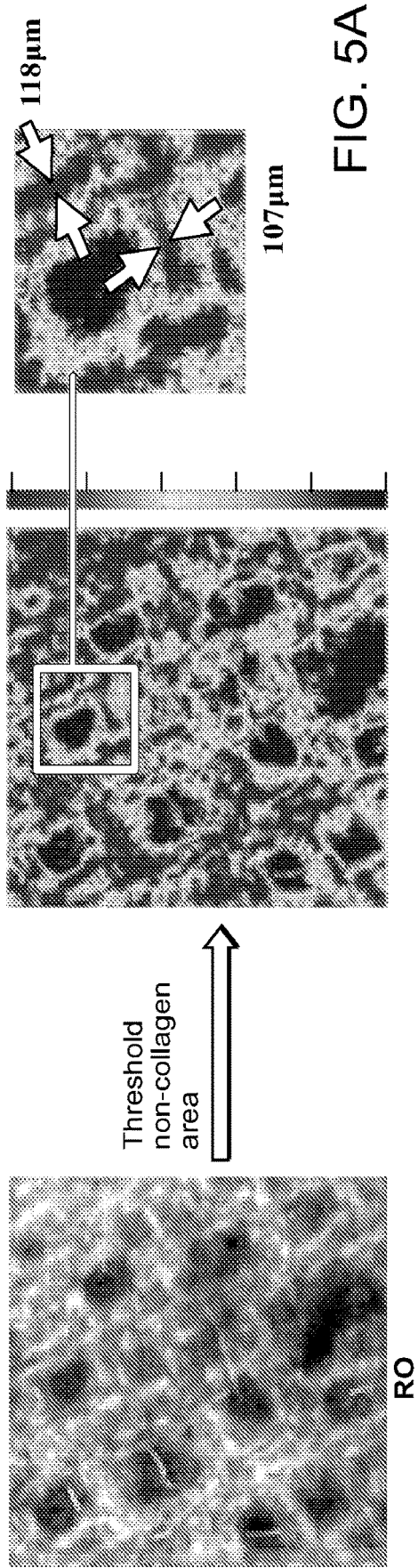
FIGS. 5A-5B illustrate images that are processed to generate quantitative data in accordance with preferred embodiments of the invention.
Figure 5B:
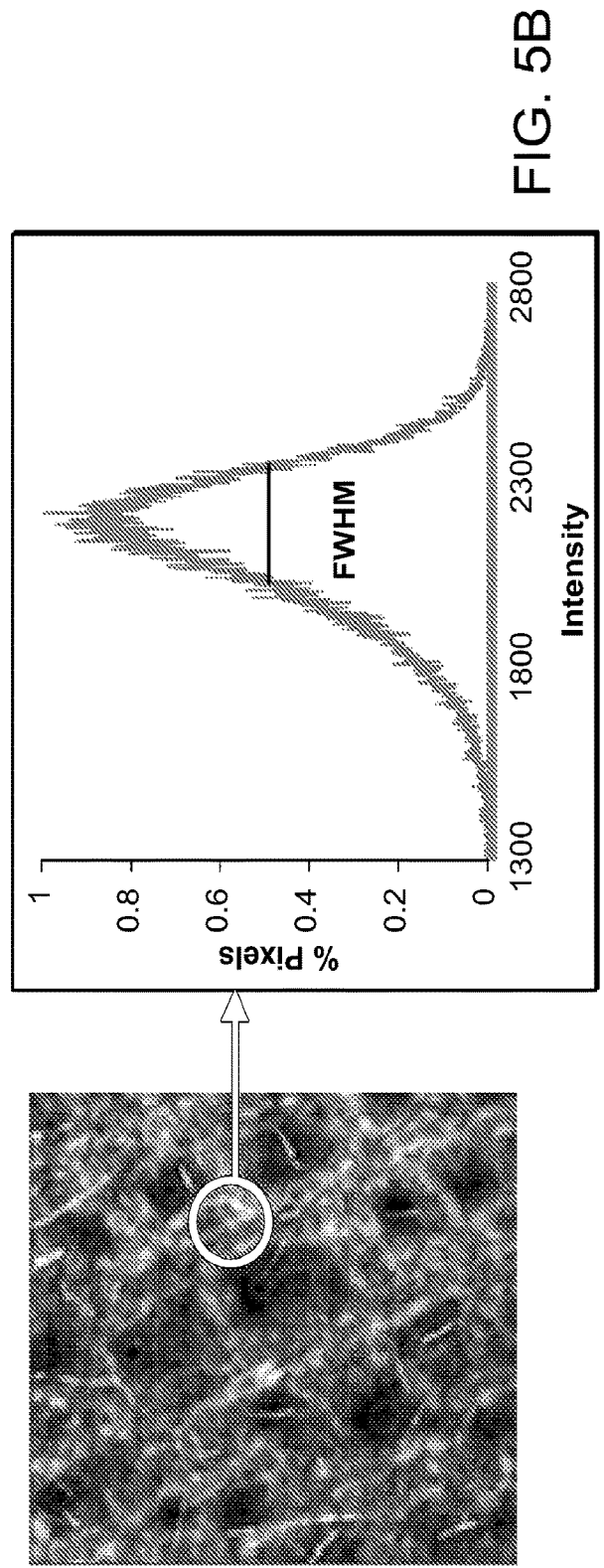

FIG. 5A illustrates examples of thresholded region of interest (ROI) images. FIG. 5B illustrates an intensity histogram of collagen bundles illustrated in FIG. 5A. From threshold image 2 collagen bundle size and percentage collagen area were measured. The collagen bundle diameter obtained from the threshold image is approximately 110 μm, which is consistent with sizes reported from historical studies. In some embodiments, the collagen bundle diameter is used to determine the proper thresholding level.

Figure 10A:
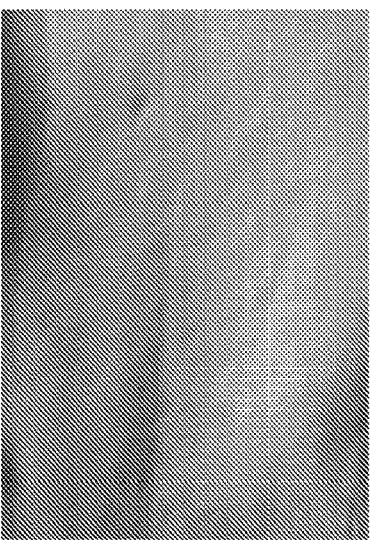
FIGS. 10A-10F show both digital pictures and wide-field ROI images of various subjects.
Figure 10B:
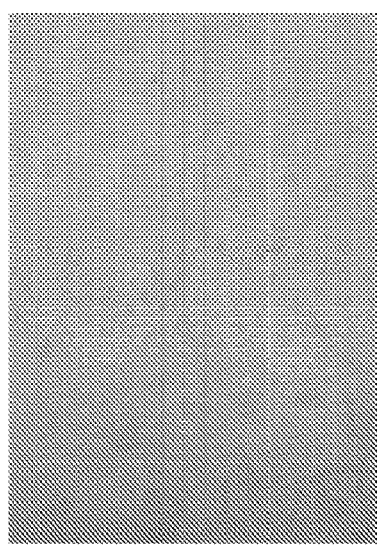
Figure 10C:
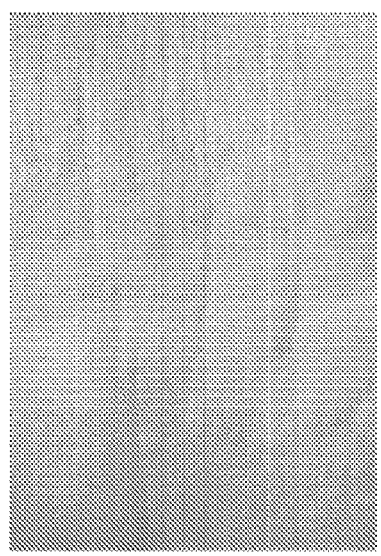
Figure 10D:
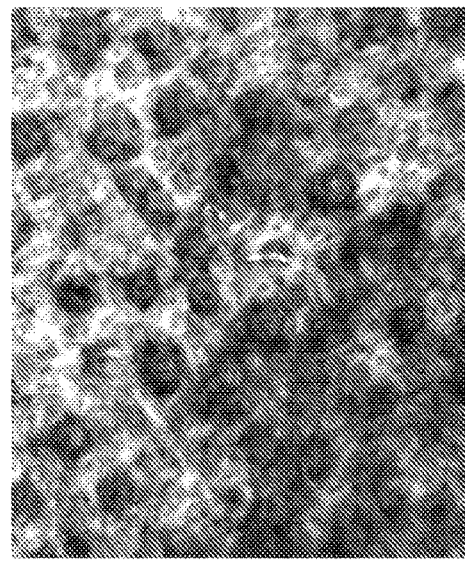
Figure 10E:
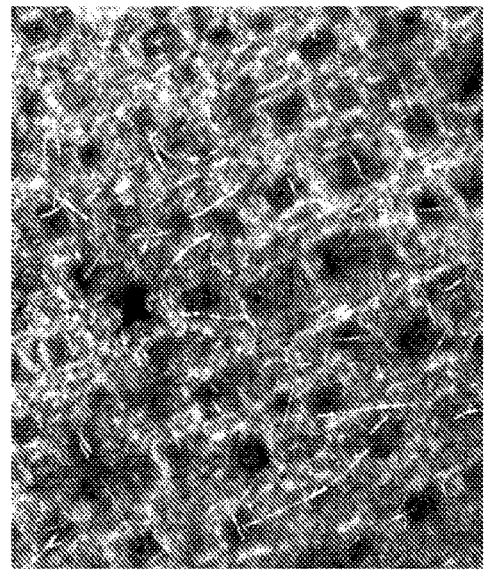
Figure 10F:
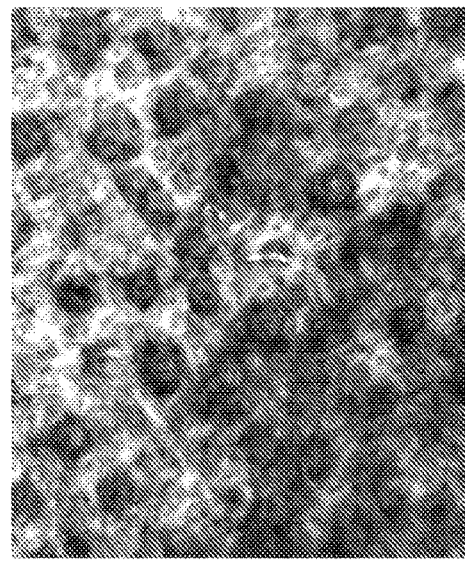

Percentage collagen area, normalized average pixel value of collagen and normalized the full width at half maximum (FWHM) of the intensity histogram (see FIG. 5B) of collagen bundles for subjects in three age groups are summarized in Table 1. Age group A (28-31 years of age) shows the highest average collagen area, which is 19% higher than age group B (35-40 years of age) and 39% higher than age group C (50-65 years of age). Normalized average pixel value, which indicates both the density and compactness of the collagen bundles, also shows a maximum value in age group A, and decreased by 5% and 8% in age group B and C respectively. Data from immunohistochemical measurements comparing the relative quantity of type I and type III collagen from facial skin of subjects ranging from 10 to 80 years old is shown in Table 2. As illustrated by Table 2, decreasing of the intensity of immune stained collagen with age is consistent with the results obtained from the imaging device described herein. In contrast to the immunohistochemical measurements, which used antibodies to investigate the type I and type III collagen, the method of imaging described here enables quantification of the overall collagen density from the image itself. In contrast to the percentage collagen area, this analysis indicates that normalized FWHM of the intensity histogram of age group A is lower than that of age group B and C by 22% and 25% respectively. The increase of FWHM value in skin of the oldest group of patients indicates the decreasing of compactness and reflectivity of the collagen bundles. In younger subjects, the collagen network is more compact, and the space between collagen bundles can hardly be seen in the image. Most collagen bundles have high reflectivity as shown in FIGS. 10A-10F (described below in detail). Histograms of the images are sharp and narrow, which leads to low FWHM. However in elderly subjects, collagen network starts to become sparse. The space between collagen bundles appears as dark grey in the image. Part of the collagen bundles still preserve high reflectivity while some show low reflectivity. Both the collagen bundles with low reflectivity and degenerated collagen structures appear as dark gray pixels in the image, which results in the broader intensity histogram with long tail and higher FWHM. Increased FWHM in senior skin can be measured using second harmonic generation measurements of human facial skin. The various differences in characteristics between young and senior skin can be seen in the images in FIGS. 10A-10F. Note that FIGS. 10A and 10D are images of 25 year old subjects, FIGS. 10B and 10E are images of 35 year old subjects, and FIGS. 10C and 10D are images of 65 year old subjects.

FIGS. 6A-C and 7A-C show example images of 24 and 43 year old subjects, respectively. FIGS. 6 and 7 show a digital picture (A) of the skin surface, processed polarization enhanced wide-field reflectance image (B), and four regions of interest (C) for each subject. In the 440 nm wide-field reflectance image of the 24 year old subject (FIG. 6B), collagen bundles appear bright due to scattering and the spaces in between collagen bundles appear dark, which strengthens the contrast of collagen area. The smaller ROIs with field of view 5 mm×5 mm preserve resolution of 12 μm, which enables quantitative analysis of collagen structure and density. To evaluate dermal structure, the system generates data to evaluate collagen area, the full width at half maximum (FWHM) of the intensity histogram (see FIG. 5B), as well as normalized average pixel values. To enable comparison between the subjects, all the images were normalized using calibrated reflectance reference. Histograms of the normalized ROI images were calculated a graphed and their full width at half maximum values (FWHM) were determined using the formula presented below, $$f(x) = \frac{1}{\sigma\sqrt{2\pi}} \exp\left[-\frac{(x-x_0)^2}{2\sigma^2}\right]$$

$$FWHM = 2\sqrt{2\ln 2}\,\sigma \approx 2.3548200\,\sigma.$$

Normalized ROI images were thresholded to about 35% to 40% brightness. Threshold values were recorded to define percentage collagen area.

Then parameters obtained from different ROIs were averaged over each subject. We summarized the data for each subject and the results demonstrated large variance for subjects of different ages (Shown in FIGS. 6A-C, 7A-C and Table 1). As shown in FIGS. 6-7, collagen area, representing collagen density and content, decreases with age, whereas full width at half maximum value, indicating compactness of collagen bundles, increases with age.

TABLE 1

Quantitative Analysis of Collagen. Group A - 7 subjects; group B - 6 subjects; Group C - 3 subjects. Skin types I-III.

| | averaged values | | |
|---|---|---|---|
| | group A 28-31 | group B 35-40 | group C 50-65 |
| area occupied by collagen, % | 1 | 0.84 | 0.75 |
| normalized APV of collagen | 1 | 0.95 | 0.92 |
| normalized FWHM | 0.75 | 0.97 | 1 |

TABLE 2

Data from immunohistochemical studies comparing the relative quantity of collagen from subjects ranging from 10 to 80 years old, represented by nth decade of age.

| Age (decades) | $3^{rd}$ | $4^{th}$ | $5^{th}$ | $6^{th}$ | $7^{th}$ |
|---|---|---|---|---|---|
| Relative quantity of collagen | 1.0 | 1.1 | 0.78 | 0.81 | 0.63 |

Figure 8A:
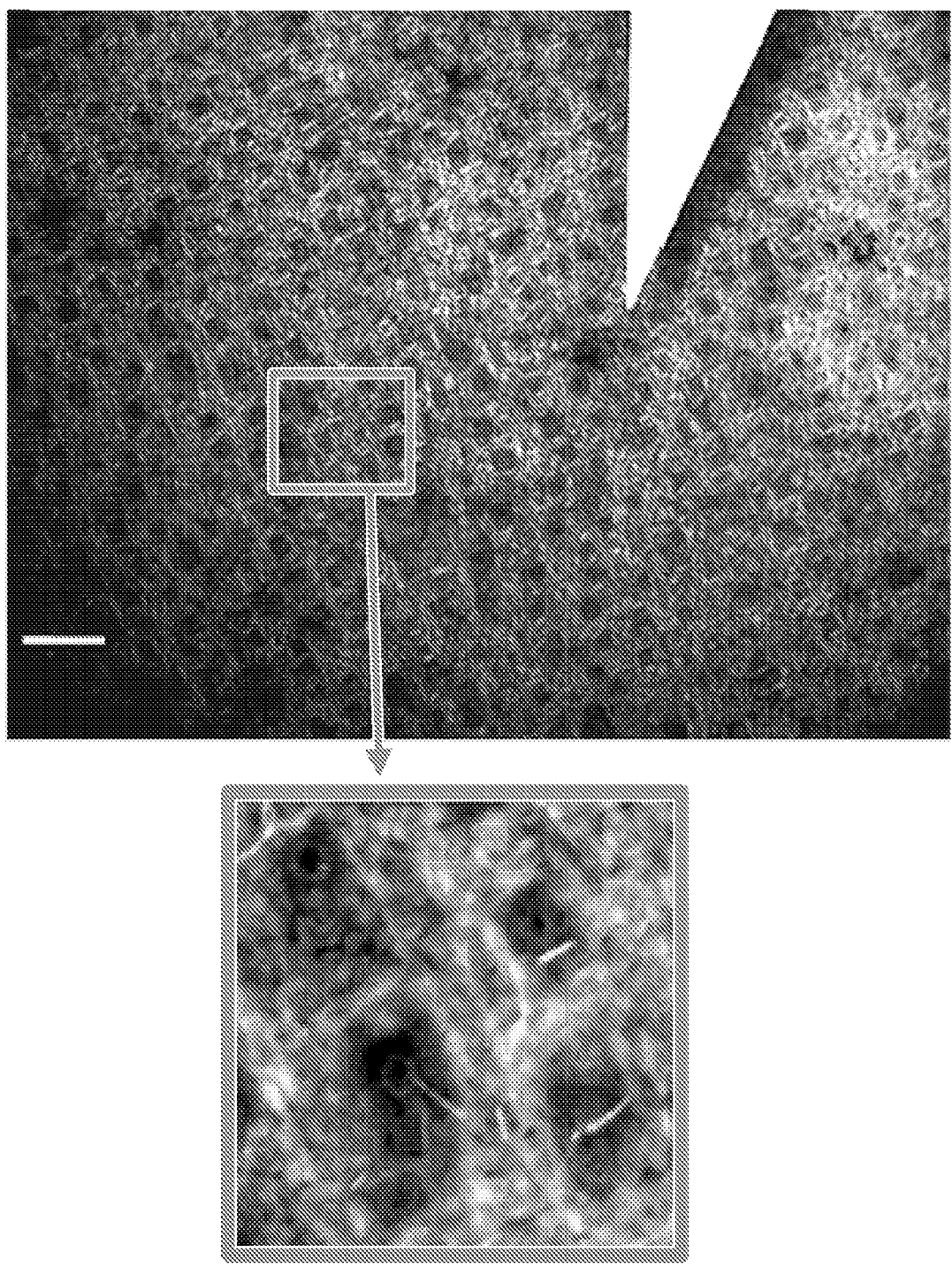
FIGS. 8A-8B are a comparison of collagen structure revealed by in vivo noninvasive polarization reflectance macro-imaging and ex vivo reflectance confocal imaging.
Figure 8B:
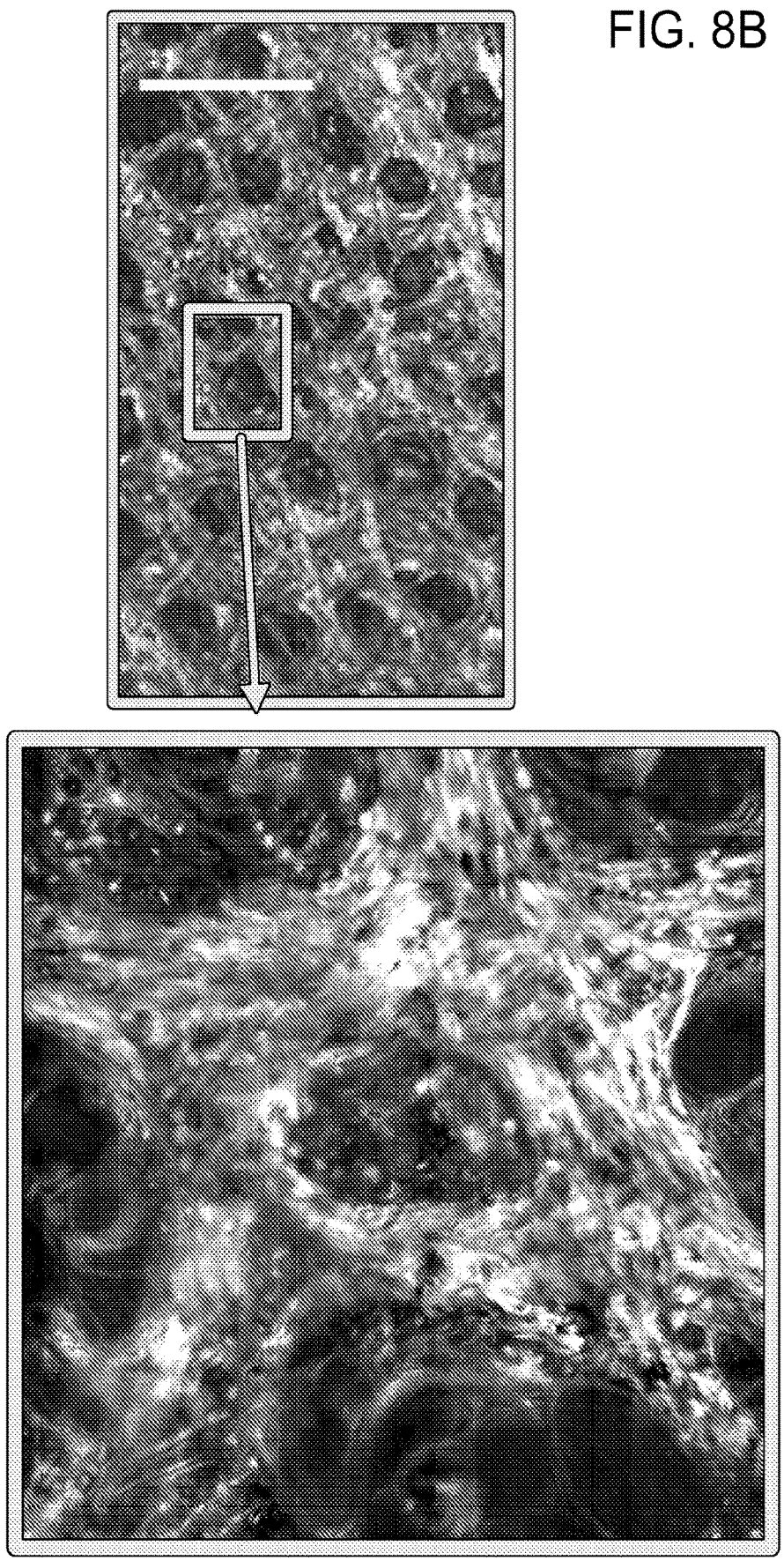
Figure 9A:
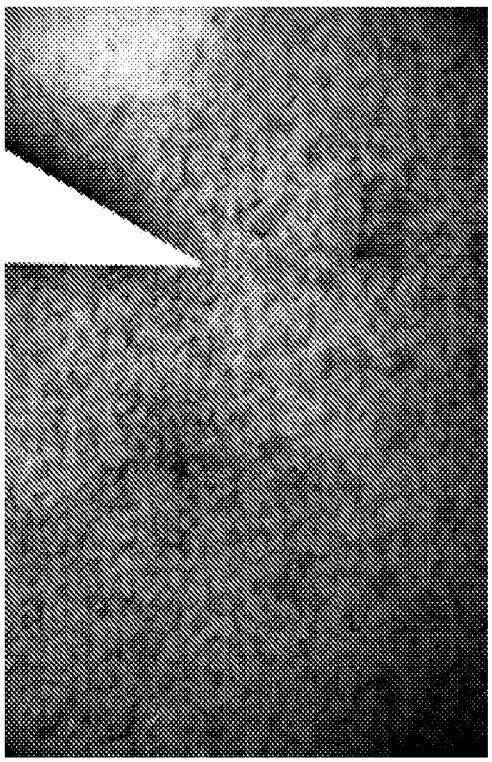
FIG. 9A-9D show images of a region including a collagen image, an image of blood, a reference image and a photograph of the skin surface, respectively.
Figure 9B:
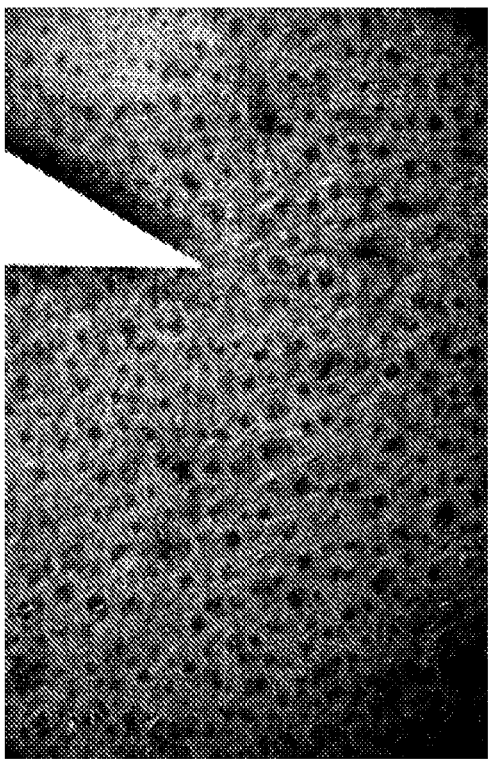
Figure 9C:
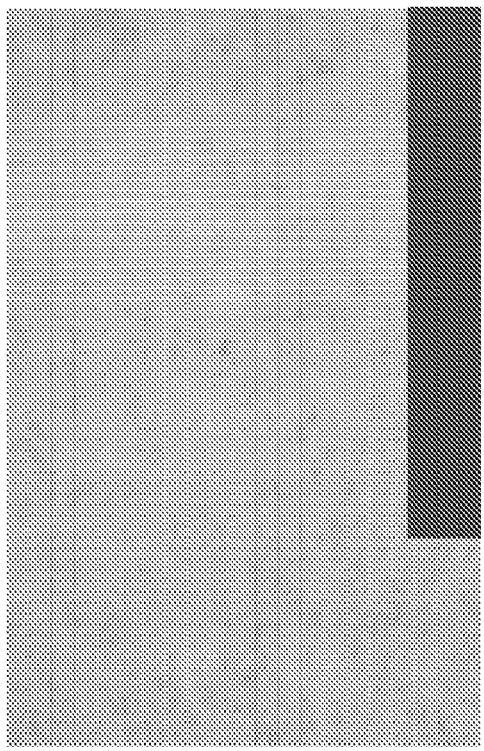
Figure 9D:
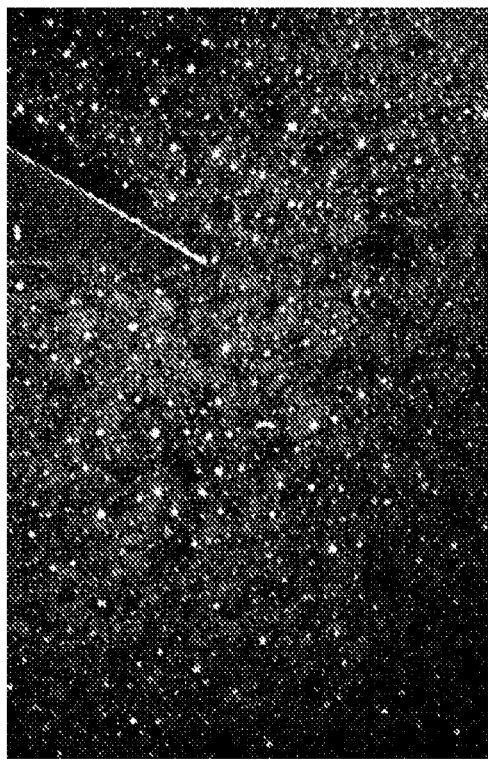

To further characterize the data, a biopsy from the imaged site of one of the subjects provide an excised tissue sample and confocal reflectance images (785 nm) were acquired from the dermal side of the biopsy. The results of comparison of macro-imaging and confocal imaging are presented in FIGS. 8A and 8B, respectively. They demonstrate similarities in the appearance of collagen network. Confocal mosaic was used as a reference to show the performance of the polarization enhanced wide-field system described herein. FIG. 8A shows in vivo wide-field reflectance images at 440 nm and FIG. 8B shows ex vivo confocal mosaics reflectance images of collagen. The confocal mosaic was acquired from adjacent single images of the dermal side of the ex vivo skin tissue. The confocal image illustrates the network of collagen fibrils and collagen bundles. Wide-field reflectance images showed the same pattern of the collagen network as the confocal mosaics, indicating that the in vivo wide-field image at 440 nm is able to monitor the same level of skin layer as the ex vivo confocal microscopy. With a resolution of 12 μm, the wide-field image delineates the dermal network with the quantified distribution and characteristics of tissue morphology such as collagen bundles and hair follicles.

Detecting cross polarized light remitted from skin allowed for adjusting depth of imaging and rejecting signal from epidermal structures. Depending on the wavelength, as well as type and optical properties of skin, the depth from which images were acquired can vary between about 50 and about 200 microns. The images can emphasize different skin structures, such as collagen or blood as shown in the photographs in (FIGS. 9A-9D). Fluorescence images can also be obtained to provide additional information regarding distribution of tissue components.

In FIGS. 10A-10F both, digital pictures and wide-field ROI images, of subjects from three age groups with age 25, 35 and 65 years old are shown. The digital pictures provide a macroscopic view of the imaging area, and they do not show significant differences between the three subjects, whereas the wide-field ROI image shows distinct variations between subjects with increasing age, indicating a change in density and compactness of the collagen bundles. In the wide-field image of the 25 year old subject (FIG. 10D), the collagen area consists of abundant fine collagen fibers with high reflectivity. The collagen network appears homogeneous and compact over the field of view. The image clearly delineates the margin of collagen bundles and shows high contrast between collagen and non-collagen areas. In the 35 year old subject (FIG. 10E), the collagen area still preserves a structure, but the overall reflectivity of collagen bundles is reduced in comparison with the younger subject. Interspace between collagen bundles is increased due to the lower collagen density. Some coarse collagen fibers can be seen in the image. The increase of the coarse collagen fibers in senior skin is also present in second harmonic generation measurements. In the image of the 65 years old subject (FIG. 10F), the left corner of the image (outlined in black) appears dark grey where the collagen structure is lost. The loss of collagen network appearing in the wide-field image cannot be seen in the macroscopic view. Lower contrast between collagen and non-collagen areas and the dark appearance of the collagen area may indicate the degradation of collagen bundles.

FIGS. 11A-11F show both reflectance and fluorescence images of the various subjects in the different age groups. FIGS. 12A-12F are images of different aged patients having images that are at least 15 mm² in area or larger preferably imaging regions having an area of at least 2 cm² and more preferably at least 4 cm², thus demonstrating the wide field of view capability of preferred embodiments of the invention.

Figure 13:
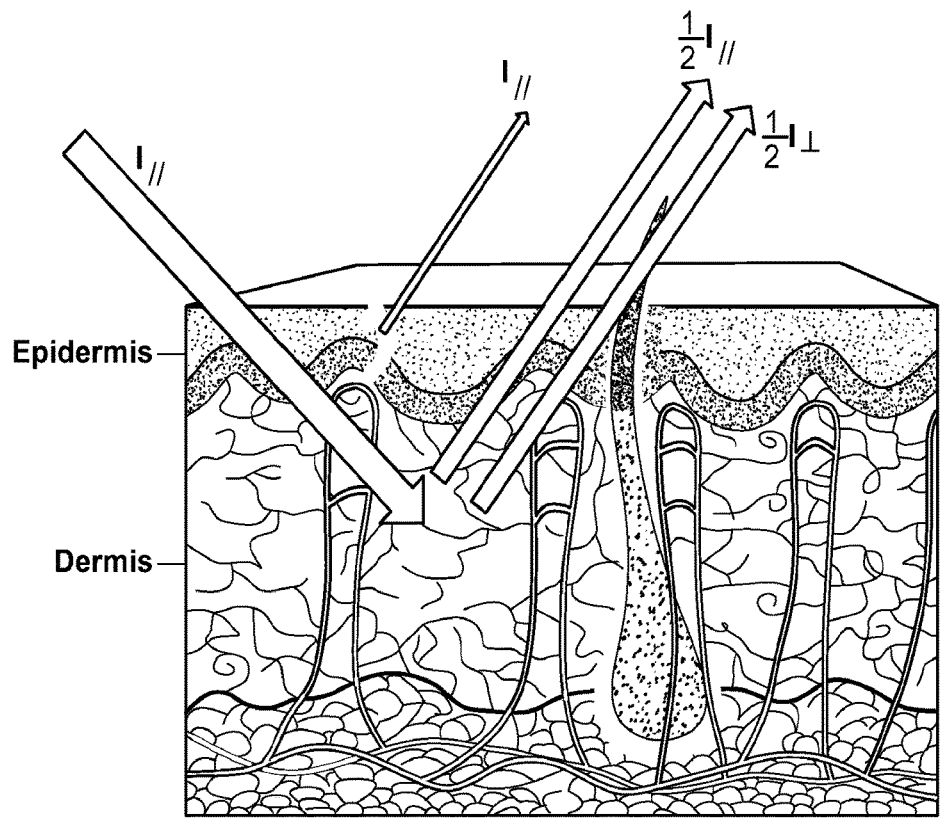
FIG. 13 is a schematic illustrating the effect of polarized light being directed onto a skin surface.
Figure 14:
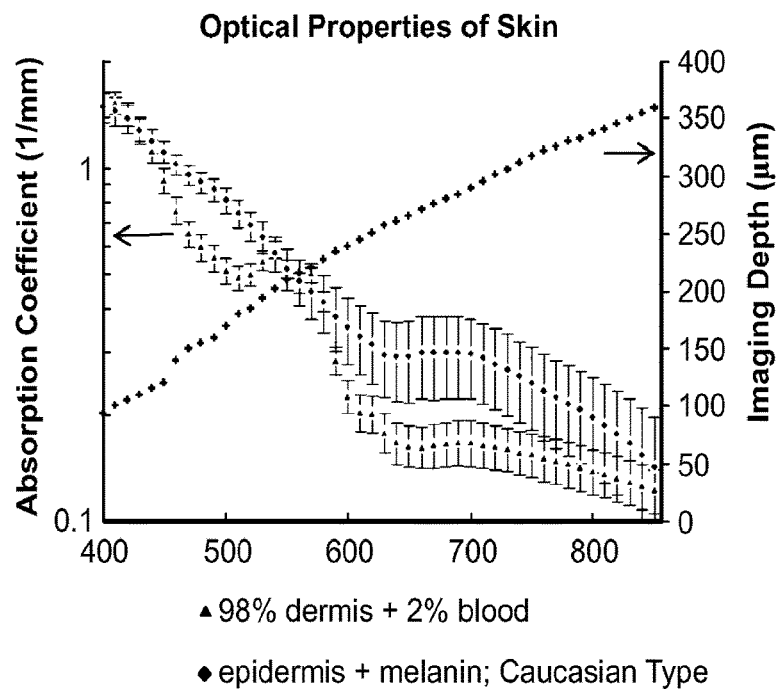
FIG. 14 is a chart illustrating the in vivo absorption of dermis, according to an embodiment.

FIG. 13 is a schematic illustrating the effect of linear polarized light being directed onto a skin surface. As shown in FIG. 13, linear polarized incident light is delivered to the skin (epidermis). As a result, co-polarized scattered light is reflected from the epidermis, and random polarized scattered light rays are reflected from the dermis (deeper skin layers). To obtain the polarized enhanced images of the deeper layers of skin, the light/signal from the upper skin layers are eliminated. When applying the linear polarized incident light, back-scattered light from the upper skin layers keeps the same polarization as the incident light due to single scattering events. However, as light goes deeper into the tissue, back-scattered light becomes randomly polarized after multiple scattering events. By taking cross-polarized images, most signals of single scattered light from epidermis and melanin are rejected, increasing the signal to noise level associated with collagen structures. Light will be attenuated in the tissue depending on the optical properties of the medium, such as absorption and scattering. Between wavelengths of 400 nm and 850 nm, scattering dominates absorption as the main mechanism of attenuation. The imaging depth in tissue is defined as $D=1/\mu_s(1-g)$, where $\mu_s$ is the scattering coefficient and g is the anisotropy factor. In some embodiments, a modified scattering coefficient can be used to approximate the attenuation of both the epidermis layer and the and dermis layer. The modified scattering coefficient can be determined by averaging the reduced scattering coefficients of epidermis and dermis. The imaging depth between wavelengths of 400 nm and 850 nm are calculated and graphed as shown in FIG. 14. Imaging depths corresponding to the four wavelengths used by the wide-field system are shown in Table 3 below.

TABLE 3

Imaging Depth Calculated for Various Wavelengths

| Wavelength | $\mu'_s$(1/mm) | Image below |
|---|---|---|
| 410 nm | 10.3 | 100 (±10) μm |
| 440 nm | 8.70 | 115 (±11) μm |

TABLE 3-continued

Imaging Depth Calculated for Various Wavelengths

| Wavelength | $\mu'_s$(1/mm) | Image below |
|---|---|---|
| 570 nm | 4.52 | 220 (±25) μm |
| 650 nm | 3.76 | 270 (±31) μm |

At 410 nm, tissue below 100 μm is imaged, at 440 nm tissue below 115 μm is imaged and at 650 nm tissue below 266 μm is imaged. These wavelengths allow for imaging the dermis layer, as the total thickness of stratum corneum and the epidermis layer is approximately 100 μm on average over the human body, even thinner on the facial skin. Absorption in human skin depends on two main chromophores: melanin and hemoglobin. Melanin is produced in epidermis and resides above the basal layers in healthy skin. By taking cross-polarized images, the signal from melanin can be reduced. Hemoglobin from blood mostly resides in the dermis layer. Healthy human dermis layer contains approximately 2% of blood. In vivo absorption spectra of epidermis and dermis between wavelengths of 400 nm and 800 nm are also shown in the graph in FIG. 14. Absorption coefficients at the four wavelengths that can be used by the wide-field system are shown in Table 3.

Figure 15:
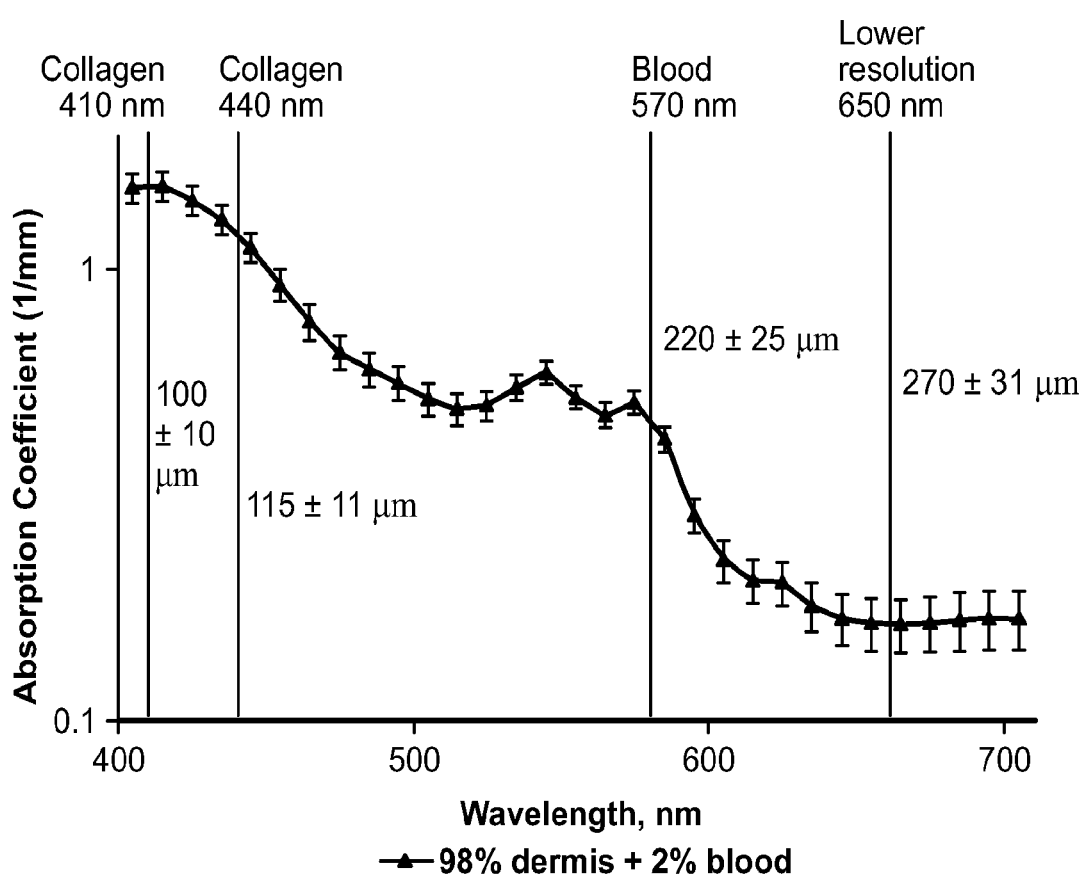
FIG. 15 is a chart illustrating the optical properties of tissue and the dermis absorption coefficient, according to an embodiment.

In some embodiments, the following in vivo absorption of dermis can be calculated by adding 2% blood and 98% ex vivo dermis:

$$\mu_{a,di}(\lambda)=2\%\times\mu_{a,b}(\lambda)+98\%\times\mu_{a,de}(\lambda)$$

where $\mu_{a,di}(\lambda)$ is the absorption coefficient for in vivo skin dermis at wavelength $\lambda$, $\mu_{a,b}(\lambda)$ is the absorption coefficient of human blood (hematocrit=44%, 0.3 Osmolality, pH=7.4) at wavelength $\lambda$ and $\mu_{a,de}(\lambda)$ is the absorption coefficient for ex vivo dermis. As shown in FIG. 14, the double-peaked spectra feature around 550 nm corresponds to the blood absorption band. The absorption peak of blood at 570 nm makes it suitable for monitoring vasculature, but not collagen structures. At a wavelength of 650 nm, image resolution is lower than shorter wavelengths due to the scattering from the bulk tissue. Both images of 410 nm and 440 nm provide proper imaging depth, with lower signal levels from blood and better resolution. However, a wavelength of 410 nm has comparatively higher scattering, which may lead to lower signal to noise ratio than the wavelength of 440 nm. Based on the optical properties of skin between the four wavelengths, cross-polarized reflectance images at 440 nm were used for evaluation of collagen structures. FIG. 15 is a chart illustrating the dermis absorption coefficient for various wavelengths that may be calculated using the formula discussed above.

To enable quantitative assessment of the images and comparison between different subjects, a calibrated reflectance standard (12%-15% for wavelengths in the range of 390 nm-750 nm) was imaged together with the skin area. Images were then calibrated and normalized with the reflectance standard in the field of view. With the reflectivity of the reference and the measured pixel values, absolute reflectance of each single pixel can be calculated and calibrated by the formula $$R^\lambda_{i,j} = \frac{PXL^\lambda_{i,j}}{PXL^\lambda_{i,j,ave}} \times R^\lambda_s$$

where i, j stand for pixel matrix, $\lambda$ is the wavelength, $R^{\lambda}_{i,j}$ is the reflectivity of the single pixel (i, j) at wavelength $\lambda$; $PXL^{\lambda}_{i,j}$ is the pixel value of the single pixel (i, j) at wavelength $\lambda$; $PXL^{\lambda}_{s,ave}$ is the average pixel value of the reference area; $R^{\lambda}_s$ is the reflectivity of the standard reference at wavelength $\lambda$.

Image normalization is the basis for quantitative analysis and enables comparison between different subjects and different images. For each normalized image, low pass and sharpen filters may be carried out with an image processing software to reduce noise and the impact of scattering from the lower skin layers. From each processed image, 4-5 regions of interest (ROIs) of 5 mm×5 mm were selected for evaluation.

FIGS. 16A-16F show images that illustrate the presently disclosed polarized wide-field imaging technique and other techniques that help in evaluating collagen in various subjects. FIGS. 16A and 16B are images of collagen from a young subject and a senior subject, respectively, taken using the polarized wide-filed imaging technique described herein. FIGS. 16C and 16D are images of collagen from a young subject and a senior subject, respectively, taken using the second harmonic generation technique. FIGS. 16E and 16F are images of collagen from a young subject and a senior subject, respectively, taken using the immunohistochemical technique. FIGS. 16A-16F allows for a comparison between the various techniques, and show the loss of collagen in the senior subject versus the young subject.

Figure 17A:
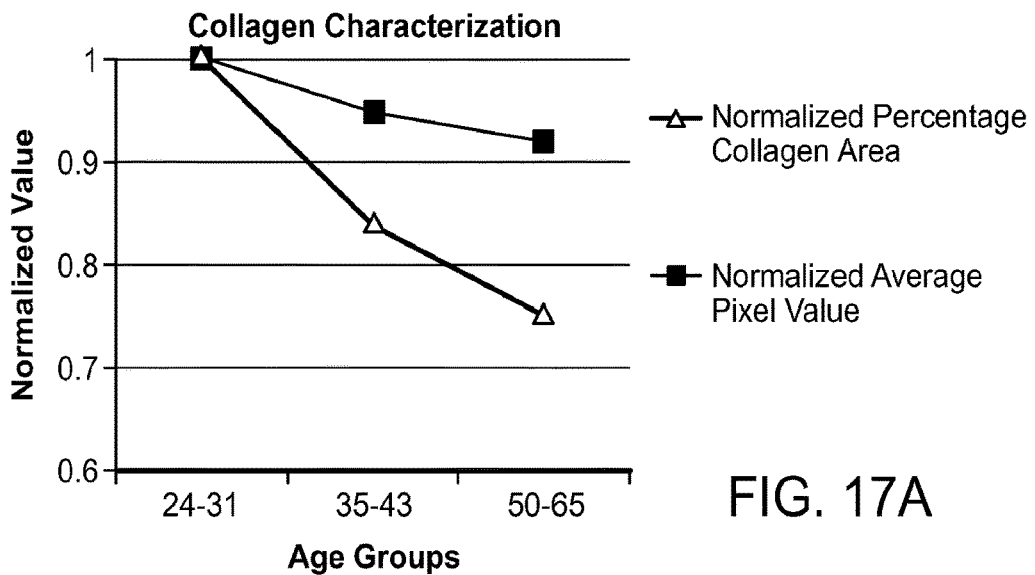
FIGS. 17A-17B are charts illustrating various quantifiable measurements of the collagen structure from different subjects.

FIG. 17A is a chart illustrating collagen structure vs. age determined using the polarized wide-field imaging technique. The values used for this chart are shown in Table 4.

TABLE 4

Percentage of Collagen Area and Normalized APV for various age groups.

| Age Group | A (24-31) | B (35-43) | C (50-65) |
| --- | --- | --- | --- |
| % Collagen Area | 1 | 0.84 | 0.75 |
| Normalized APV | 1 | 0.95 | 0.92 |

Figure 17B:
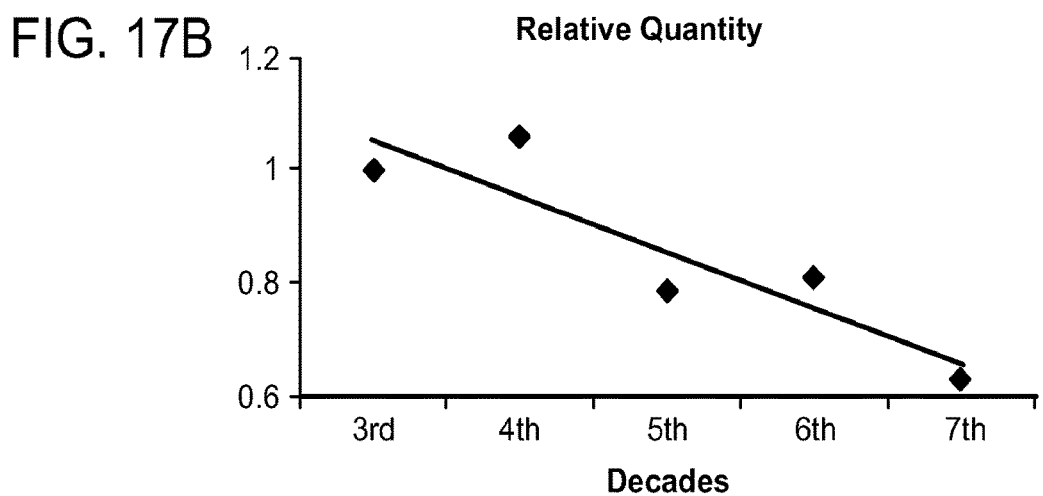

FIG. 17B is a chart illustrating the relative quantity of collagen based on age using an immunohistochemical analysis. The values used for this chart are shown in Table 5.

TABLE 5

Relative quantity of collagen determined from an immunohistochemical study

| Age (decades) | $3^{rd}$ | $4^{th}$ | $5^{th}$ | $6^{th}$ | $7^{th}$ |
| --- | --- | --- | --- | --- | --- |
| Relative quantity of collagen | 1.0 | 1.1 | 0.78 | 0.81 | 0.63 |

Both charts in FIGS. 17A and 17B show a decrease in collagen density with an increase in age.

Figure 18:
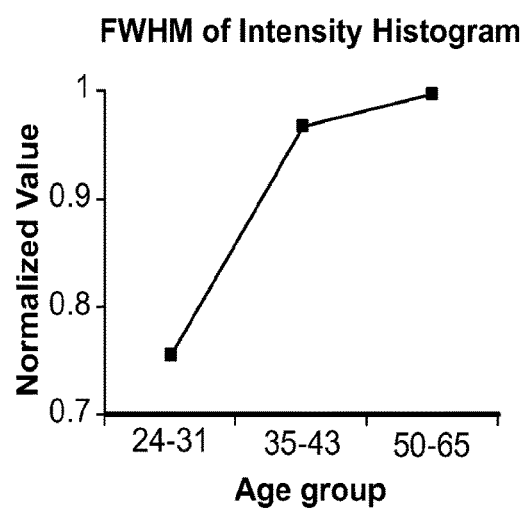
FIG. 18 is a chart illustrating the FWHM vs. age determined according to a preferred embodiment.

FIG. 18 is a chart illustrating normalized FWHM vs. age determined using the polarized wide-field imaging technique. The values used for this chart are shown in Table 6. The chart shows an increase in the FWHM with age. This finding is consistent with results from measurements using the second harmonic generation.

TABLE 6

Normalized FWHM for various age groups determined using polarized wide-field imaging

| Age Group | A (24-31) | B (35-43) | C (50-65) |
| --- | --- | --- | --- |
| Normalized FWHM | 0.75 | 0.97 | 1 |

The in vivo imaging method provides resolution with a large field of view of at least 1 cm$^2$ and preferably at least 8 cm$^2$ or more. In a preferred embodiment, a 3 cm×3 cm image is obtained at each depth. The images enable viewing of collagen bundles and detailed dermal structures. Histopathological analysis is the standard for clinical diagnosis, but requires biopsy and can neither be done in vivo nor in real time. The present imaging method provides rapid non-invasive assessment of large skin areas in vivo and is entirely harmless and nonintrusive. Compared to microscopy techniques, such as confocal, two photon and second harmonic, the present imaging method provides orders of magnitude larger field of view combined with a lateral resolution of at least 15 µm and high signal to noise ratio, and does not require expensive components and high power densities of light exposure or laser sources.

Laser non-ablative fractional treatment (NAFT) has become available in a home-use setting due to advent of self-application NAFT devices. In this mode of treatment, in contrast to a typical in-office procedure, fractional coverage is gradually accumulated over a period of time through frequent (e.g., daily) applications. Polarization-enhanced multi-spectral imaging as described herein can be used to observe and monitor effects of the home-administered NAFT on collagen-elastin dermal networks.

Subjects with peri-orbital wrinkles used a commercially available NAFT device (PaloVia® Skin Renewing Laser, Palomar Medical Technologies Inc., Burlington, Mass.) according to recommended daily treatment regimen. Wide-field reflectance images of both co-polarization and cross-polarization were acquired between 390 and 750 nm. The images were analyzed with a software module in which collagen density, full width at half maximum of image histograms (FWHM IH) and normalized averaged pixel values were calculated to characterize dermal structure.

The images showed detailed dermal structures such as the collagen-elastin network, blood vessel system, and hair follicles. Different collagen network patterns were observed for patients of different age groups. FWHM IH and collagen density data were summarized and used to quantify collagen content. Data analysis at two-week timepoint after treatment revealed increase in collagen content and ordering of the collagen-elastin network as a result of the treatments. Polarization-enhanced multi-spectral imaging is a useful non-invasive evaluation tool, allowing the monitoring of changes in dermal structure caused by non-ablative fractional treatments.

TABLE 7

| Age Group | Treatment | Collagen Area % | Percentage Improvement % |
| --- | --- | --- | --- |
| A (24-25) | pre | 0.91 | 9.89 |
|  | post | 1 |  |
| B (43) | pre | 0.7 | 24.29 |
|  | post | 0.87 |  |
| C(50-53) | pre | 0.67 | 7.46 |
|  | post | 0.72 |  |

Figure 20B:
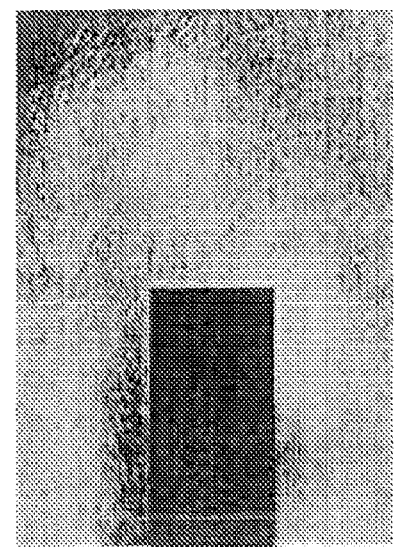
FIGS. 20A-20B are images of the skin of a patient after treatment.
Figure 20A:
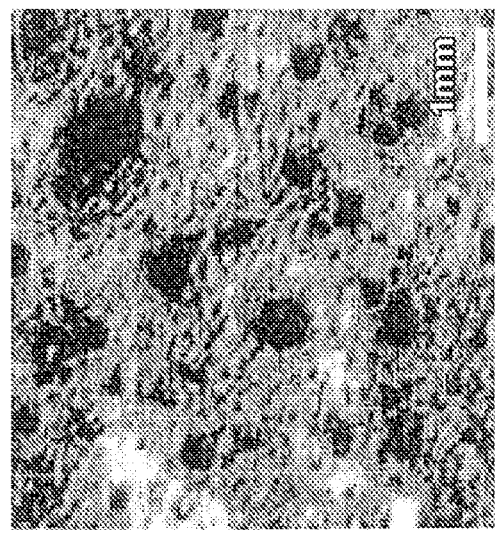
Figure 19:
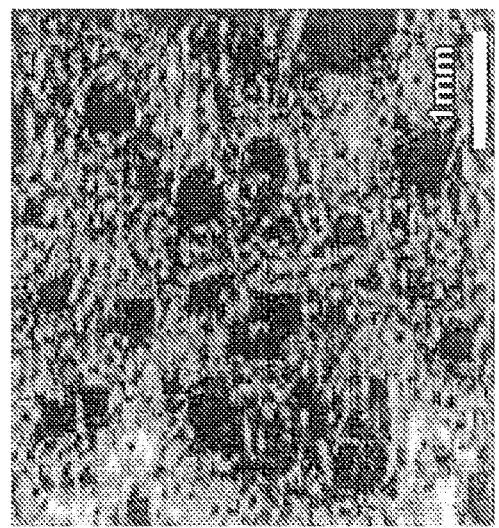
FIG. 19 is an image of the skin prior to treatment.

Shown in FIG. 19 is an image of collagen of the shin surface prior to treatment. After treatment an image was taken of the same area and is shown in FIG. 20A. The area of treatment is seen in FIG. 20B and demonstrates a substantial increase in the collagen area as a result of the treatment that is seen in Table 7.

Age-related changes of facial collagen structure have been measured with different modalities. The immunohistochemical method uses transmission electron microscopy to investigate the skin collagen, which shows the fragmentation of fibers and decreased collagen density by the 6th and 7th decade. Confocal laser scanning microscopy and optical coherence tomography can be used to investigate the age-related dermal changes in location and structure of collagen fibers in vivo. These techniques indicate that younger skin consists of relatively thicker collagen bundles than the senior skin. Second harmonic generation microscope images show that thin collagen fibers greatly reduced in elderly subjects, and coarse collagen fiber appears in senior skin. These collagen structural changes can also be seen from the wide-field images described herein. A polarization-sensitive OCT methodology for imaging collagen shows age-dependent decrease in the birefringence of the cheek collagen. These changes in structure, abundance and birefringence of collagen indicate the degeneration and disorganization of collagen fiber in senior skin, which are also indicated by the wide-field images described herein. The polarization enhanced multispectral wide-field imaging of the present disclosure enables in vivo noninvasive visualization of human dermal structure. Image analyses of collagen density, normalized average pixel value and FWHM show important physiological parameters that reveal the differences in skin with increasing age.

Preferred embodiments of the present invention provide a polarization enhanced multispectral wide-field reflectance imaging method that is suitable for noninvasive in vivo assessment of dermal structure. Reflectance skin images of subjects between 24 and 65 years old were acquired and analyzed. In comparison with clinical studies that often take several months to complete, the imaging technique described here enables real-time image acquisition and analysis. It enables the rapid overview of a large skin area up to 5×5 cm² without biopsy or laser exposure. The present disclosed system is sensitive to dermal structural differences and provides accurate diagnostic information for subjects with skin type I to III.

While the present invention has been described here in conjunction with certain preferred embodiments, a person with ordinary skill in the art, after reading the foregoing specification, can effect changes, substitutions of equivalents and other alterations to the systems and methods described herein. Each embodiment described above can also have included or incorporated therewith such variation as disclosed in regard to any and all of the other embodiments. Thus, it is intended that the scope of the claims granted herewith be limited in breadth only by definition as defined in the specification and appended claims and any equivalents thereof.

The invention claimed is:

1. A method for imaging and evaluating collagen structure in a region of tissue of a patient in vivo without staining in real time, the method comprising the steps of:
   illuminating a region of skin in vivo on a patient with light, the region having a surface area defined by an imaging aperture;
   detecting cross polarized images of light reflected by the region of tissue with a detector separated at a distance from a skin surface, the detector generating image data representing a first depth and a second depth at respective first and second discrete illumination wavelengths in which the collagen structure appears, wherein the second depth is deeper than the first depth and a difference between the first and second wavelengths is at least 10 nm;
   evaluating the image data to select only one of the first or second wavelengths of the light in which the collagen structure appears in the respective image data;
   processing, by a data processor, the image data in which the collagen structure appears with reference data to determine at least one quantitative characteristic selected from reflectivity, content, density and bundle size of the collagen structure in the region of tissue;
   forming and presenting, by the data processor, a chart of the at least one quantitative characteristic on a display; and
   evaluating the region of tissue by review of the chart of the at least one quantitative characteristic.

2. The method of claim 1 further comprising illuminating the imaging aperture having an imaging area of at least 1 cm², the imaging area being illuminated with light from a light source.

3. The method of claim 1 further comprising detecting a plurality of images at different wavelengths in a range of 390 nm to 730 nm.

4. The method of claim 1 further comprising performing a laser treatment on the region of the tissue of the patient and re-imaging the region after the laser treatment to evaluate the laser treatment.

5. The method of claim 1 further comprising detecting a cross-polarized image of the region of tissue and determining a collagen distribution with the data processor and presenting a chart of the collagen distribution.

6. The method of claim 1 further comprising determining a change in collagen distribution as a function of time from a plurality of images of a region of interest of a patient collected at a corresponding plurality of different times.

7. The method of claim 1 further comprising determining a change in reflectivity of the tissue and computing, by the data processor, a change in collagen distribution after treatment.

8. The method of claim 1 wherein the reference data includes an optical property of skin comparable to skin of the patient.

9. The method of claim 1 wherein the reference data is generated by having a calibrated reflectance standard in the field of view during imaging for calibrating and normalizing the image data, and the image data is compared with other image data.

10. The method of claim 1 wherein the second depth is beneath a dermal surface of the region of tissue in a range of 50 to 200 microns.

11. The method of claim 1 further comprising manually holding hand-held housing relative to the tissue of the patient, the housing including a detector and an illuminator: and a polarizer that polarizes the illuminating light.

12. The method of claim 11 further comprising illuminating with the illuminator that comprises an annular LED array.

13. The method of claim 1 further comprising processing image data with the data processor, applying a threshold to the image data, determining a normalized percentage collagen area as a function of time, and presenting the normalized percentage of collagen as a chart.

14. The method of claim 13 further comprising determining a normalized average pixel value of the image data for an age group and skin type comparable to an age and skin type of the patient.

15. A device for imaging a region of tissue without staining in real time comprising:
a housing including an imaging detector;
a light source to illuminate the region of tissue in vivo on a patient with light, the region having a surface area defined by an imaging aperture;
a polarizing element that generates a cross polarized image component that is detected with the detector and output as image data at a first depth and a second depth at respective first and second discrete illumination wavelengths in which the collagen structure appears, wherein the second depth is deeper than the first depth and a difference between the first and second wavelengths is at least 10 nm, the collagen structure appearing in the image data in only one of the first or second wavelengths; and
a data processor connected to the detector that processes the image data in which the collagen structure appears by normalizing brightness of the image data for comparison between different patients or different images and, with reference data, to determine at least one quantitative characteristic selected from reflectivity, content, density and bundle size of the collagen structure in the region of tissue,
wherein the data processor computes a collagen density distribution in the tissue and presents a chart of the collagen density distribution for evaluation.

16. The device of claim 15 wherein the housing comprises a hand-held assembly including the light source, the optical aperture and the polarizing element and the data processor generates quantitative data regarding collagen distribution in the tissue and further comprising a memory for storing images at different depths within the tissue.

17. The device of claim 15 further comprising an optical aperture having an area providing a field of view of at least 1 cm$^2$ for each image.

18. The device of claim 15 wherein the light source comprises a ring illuminator and the light source illuminates the tissue with at least the first and second discrete illumination wavelengths to image tissue at the first depth and the second depth, respectively, under the tissue surface.

19. The device of claim 15 wherein the light source illuminates a region on the tissue surface to image an area of at least 2 cm$^2$.

20. The device of claim 15 wherein the light source illuminates a region on the tissue surface to image an area of at least 4 cm$^2$.

21. The device of claim 15 further comprising a computer program stored on a non-transitory computer readable medium to process image data.

22. The device of claim 15 further comprising a light source system that illuminates the tissue at a plurality of wavelengths between 390 nm to 730 nm at different times.

23. The device of claim 15 wherein the data processor applies a threshold to the image data and determines a percentage of collagen area.

24. The device of claim 15 wherein the data processor determines a normalized pixel value for the image data.

25. A device for imaging a region of tissue in vivo without staining in real time comprising:
a housing including an imaging detector, a light source to illuminate the region of tissue;
a polarizing element that generates a cross polarized image of a depth in the range of 50 to 200 microns in the region, the cross polarized image being detected by the imaging detector and output as image data at a first depth and a second depth at respective first and second discrete illumination wavelengths in which the collagen structure appears, wherein the second depth is deeper than the first depth and a difference between the first and second wavelengths is at least 10 nm, the collagen structure appearing in the image data in only one of the first or second wavelengths: and
a data processor receiving the image data in which the collagen structure appears, wherein the data processor is operative to:
calculate absolute reflectance of each single pixel of the field of view: and quantify the collagen structure based upon the absolute reflectance of the pixels, wherein the region of tissue includes a calibrated reflectance standard and the data processor is further operative to calibrate and normalize the image data with the calibrated reflectance standard in a field of view of the imaging detector, and processes the image data in which the collagen structure appears with reference data to determine at least one quantitative characteristic selected from reflectivity, content, density and bundle size of the collagen structure in the region of tissue;
wherein the data processor presents a chart of the at least one quantitative characteristic for evaluation.

26. A device as recited in claim 25, wherein the data processor is further operative to calculate a percentage of collagen in the region.

27. A device as recited in claim 25, wherein the data processor is further operative to calculate and display a normalized full width at half maximum (FWHM) of a histogram of the reflectance for evaluation of health of the region.

28. A device as recited in claim 25, wherein the data processor is further operative to obtain fluorescence images to evaluate distribution of tissue components.

* * * * *